(12) United States Patent
Tumey et al.

(10) Patent No.: US 7,947,691 B2
(45) Date of Patent: May 24, 2011

(54) CYCLIC N-HYDROXY IMIDES AS INHIBITORS OF FLAP ENDONUCLEASE AND USES THEREOF

(75) Inventors: Lawrence N. Tumey, New Windsor, NY (US); Youssef Bennani, Shaker Heights, OH (US); Bayard Huck, University Heights, OH (US); David C. Bom, Broadview Heights, OH (US)

(73) Assignee: Athersys, Inc., Cleveland, OH (US)

( * ) Notice: Subject to any disclaimer, the term of this patent is extended or adjusted under 35 U.S.C. 154(b) by 624 days.

(21) Appl. No.: 11/632,920

(22) PCT Filed: Jul. 20, 2005

(86) PCT No.: PCT/US2005/025592
§ 371 (c)(1), (2), (4) Date: Jul. 7, 2008

(87) PCT Pub. No.: WO2006/014647
PCT Pub. Date: Feb. 9, 2006

(65) Prior Publication Data
US 2008/0287465 A1  Nov. 20, 2008

Related U.S. Application Data

(60) Provisional application No. 60/589,635, filed on Jul. 21, 2004.

(51) Int. Cl.
*C07D 495/04* (2006.01)
*C07D 491/08* (2006.01)
*A61K 31/519* (2006.01)

(52) U.S. Cl. .................................. 514/260.1; 544/278

(58) Field of Classification Search .................. 544/278; 514/260.1
See application file for complete search history.

(56) References Cited

OTHER PUBLICATIONS

Tserng et al. (Journal of Organic Chemistry (1975), 40(2), 172-5).*

\* cited by examiner

*Primary Examiner* — Bruck Kifle
(74) *Attorney, Agent, or Firm* — Wood, Phillips, Katz, Clark & Mortimer

(57) ABSTRACT

Acrylic n-hydroxy imides and their use in pharmaceutical compositions and in the inhibition of flap endonuclease are disclosed.

10 Claims, No Drawings

CYCLIC N-HYDROXY IMIDES AS INHIBITORS OF FLAP ENDONUCLEASE AND USES THEREOF

TECHNICAL FIELD

This invention relates to compounds having pharmacological activity, to compositions containing these compounds and to a method of treatment employing the compounds and compositions. More particularly, this invention concerns certain cyclic n-hydroxy imide derivatives. These compounds are inhibitors of flap endonuclease.

BACKGROUND OF THE INVENTION

Flap endonuclease-1 (FEN1) is a 43-kDa metal-dependent nuclear enzyme that exhibits both DNA structure-specific endonuclease activity and 5' exonuclease activity. Arguably, the most well studied aspect of FEN1 function is its role in the cleavage of Okazaki fragments during DNA replication, Bambara, R. A.; Murante, R. S.; Henricksen, L. A. *J. Biological Chemistry* 1997, 272, 4647-4650. However, FEN1 also acts to cleave 5' DNA flaps generated during a variety of other cellular processes including double-strand break repair, Harrington, J. J.; Lieber, M. R. *EMBO J.* 1994, 13, 1235-1246, homologous recombination, Pont, K. G.; Dawson, R. J.; Carroll, D. *EMBO J.,* 1993, 12, 23-24, and base excision repair (BER), Harrington, J. J.; Lieber, M. R. *Genes Dev.* 1994, 8, 1334-1335. BER is an important cellular mechanism for the repair of DNA damage caused by alkylating agents, Parikh, S. S.; Mol, C. D.; Hosfield, D. J.; Tainer, J. A. *Current Opinion in Structural Biology* 1999, 9, 1, 37-47.

The role of FEN1 in BER is clearly exemplified in a recent report that shows nuclease-defective FEN1 results in increased cellular sensitivity to methylmethane sulfonate (MMS), a potent DNA alkylating agent, Shibata, Y.; Nakamura, T. *J. Biological Chemistry* 2002, 277, 746-754. Sensitization to DNA damaging agents may improve the therapeutic window of classical chemotherapeutics by lowering the minimum effective dose. For a review of chemosensitization: Gesner, T. G.; Harrison, S. D., *Annual Reports in Medicinal Chemistry,* 2002, 37, 115-124. Recent reports describe several small molecule inhibitors of DNA repair proteins including poly(ADP-ribose) polymerase-1 (PARP) White, A. W.; Almassy, R.; Calvert, A. H.; Curtin, N. J.; Griffin, R. J.; Hostomsky, Z.; Maegley, K.; Newell, D. R.; Srinivasan, S.; Golding, B. T. *J. Medicinal Chemistry* 2000, 43, 4084-4097, and O[6]-alkylguanine-DNA alkyltransferase (ATase or MGMT), McElhinney, R. S.; Donnelly, D. J.; McCormick, J. E.; Kelly, J.; Watson, A. J.; Rafferty, J. A.; Elder, R. H.; Middleton, M. R.; Willington, M. A.; McMurry, B. H.; Margison, G. P. *J. Medicinal Chemistry,* 1998, 41, 5265-5271. These inhibitors are reported to potentiate the activity of various chemotherapeutic agents including temozolomide, Middleton, M. R.; Kelly, J.; Thatcher, N.; Donnelly, D. J.; McElhinney, R. S.; McMurry, B. H.; McCormick, J. E.; Margison, G. P. *Int. Journal of Cancer,* 2000, 85, 248-252, and topotecan, White, et al. In light of this recent work, we embarked on a strategy to identify selective small-molecule inhibitors of FEN1 for use as chemopotentiating agents. While FEN 1 has a role in DNA replication, the inhibition of the enzyme should not lead to cell death because yeast knockouts are viable, albeit at a slower growth rate than wild-type. Moreau, S.; Morgan, E. A.; Symington, L. S. *Genetics,* 2001, 159, 1423-1433.

FEN1 is highly homologous to a related endonuclease, xeroderma pigmentosum G (XPG), Gary, R.; Ludwig, D. L.; Cornelius, H. L.; MacInnes, M. A.; Park, J. S. *J. Biological Chem.,* 1997, 272, 24522-24529. XPG is part of a repair pathway that excises DNA containing pyrimidine dimers, a common form of damage caused by exposure to UV light. Defects in XPG are known to cause hypersensitivity to UV light, resulting in light-induced skin lesions and carcinoma, Berneburg, M.; Lehmann, A. R. *Adv. Genetics,* 2001, 43, 71-102. Therefore, selective inhibition of FEN1 over XPG is a key goal of this program.

SUMMARY OF THE INVENTION

The present invention provides, in its principal aspect, compounds of the general formula.

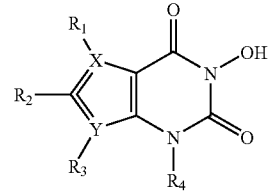

(I)

where X and Y may be C, O or S provided that one of X and Y must be C;

$R_1$ which is present when X is C is selected from the group consisting of H, aryl, heteroaryl, alkyl, alkylaryl, fused aryl with $R_2$, and fused cycloalkyl with $R_2$;

$R_2$ is selected from the group consisting of H, aryl, heteroaryl, alkyl, alkylaryl, fused aryl with $R_1$ or $R_3$, and fused cycloalkyl with $R_1$ or $R_3$;

$R_3$ which is present when Y is C is selected from the group consisting of H, aryl, heteroaryl, alkyl, alkylaryl, fused aryl with $R_2$, and fused cycloalkyl with $R_2$; and $R_4$ is selected from the group consisting of alkyl, aryl, heteroaryl and alkylaryl; and the pharmaceutically acceptable salts and isomers thereof.

This invention also provides pharmaceutical compositions comprising a pharmaceutically acceptable carrier in combination with an effective amount of at least one compound of formula (I).

The present invention also provides a method of treating conditions in which the inhibition of flap endonuclease may be of therapeutic importance such as cancer, skin growth disorders and other disorders associated with unwanted proliferation of cells comprising administering an effective amount of a compound of formula (I) to a patient in need of such treatment.

DETAILED DESCRIPTION OF THE INVENTION

Two presently preferred embodiments of the compounds of formula (I) are:

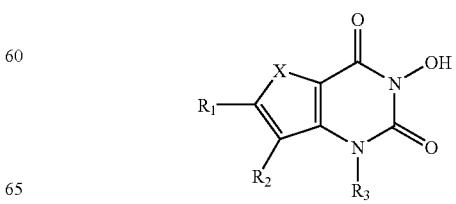

where R₁ is H, alkyl, aryl or a fused aryl or alkyl ring with R2;
R₂ is H, alkyl, aryl, or a fused aryl or allyl ring with R1;
R₃ is alkyl or aryl; and
X is S or O; and

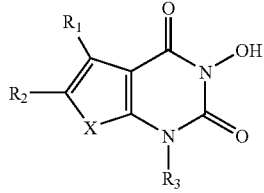

where R₁ is H, allyl, aryl or a fused aryl or alkyl ring with R₂;
R₂ is H, alkyl, aryl or a fused aryl or alkyl ring with R₁;
R₃ is alkyl or aryl; and
X is S or O.

Preferably for compounds of formula (I), X is C, Y is S, R₁ is CH₃, R₂ is H, and R₄ is substituted benzyl.

Presently preferred compounds include:
3-Hydroxy-1H-thieno[2,3-d]pyrimidine-2,4-dione;
3-Hydroxy-1,5,6,7,8,9-hexahydro-10-thia-1,3-diaza-benzo[a]azulene-2,4-dione;
1-Benzyl-3-hydroxy-5-methyl-1H-thieno[2,3-d]pyrimidine-2,4-dione;
3-Hydroxy-1-(7-methoxy-benzo[1,3]dioxol-5-ylmethyl)-5-methyl-1H-thieno[2,3-d]pyrimidine-2,4-dione;
3-Hydroxy-5-methyl-1-(2,4,5-trimethoxy-benzyl)-1H-thieno[2,3-d]pyrimidine;
1-(6-Chloro-pyridin-3-ylmethyl)-3-hydroxy-5-methyl-1H-thieno[2,3-d]pyrimidine-2,4-dione;
3-Hydroxy-5-methyl-1-quinolin-2-ylmethyl-1H-thieno[2,3-d]pyrimidine-2,4-dione;
3-Hydroxy-5-methyl-1-(2-thiophen-2-yl-thiazol-4-ylmethyl)-1H-thieno[2,3-d]pyrimidine-2,4-dione;
3-Hydroxy-1-naphthalen-2-ylmethyl-1H-thieno[2,3-d]pyrimidine-2,4-dione;
3-Hydroxy-6-phenyl-1H-thieno[3,2-d]pyrimidine-2,4-dione;
3-Hydroxy-6-phenyl-1-(tetrahydro-furan-2-ylmethyl)-1H-thieno[3,2-d]pyrimidine-2,4-dione;
3-Hydroxy-7-phenyl-1H-thieno[3,2-d]pyrimidine-2,4-dione;
1-(3-Bromo-benzyl)-3-hydroxy-1H-thieno[3,2-d]pyrimidine-2,4-dione;
3-Hydroxy-1-naphthalen-2-ylmethyl-1H-thieno[3,2-d]pyrimidine-2,4-dione;
1-(2-Chloro-benzyl)-3-hydroxy-1H-thieno[3,2-d]pyrimidine-2,4-dione;
3'-(3-Hydroxy-2,4-dioxo-3,4-dihydro-2H-thieno[3,2-d]pyrimidin-1-ylmethyl)-biphenyl-4-carboxylic acid amide;
1-(3'-Acetyl-biphenyl-3-ylmethyl)-3-hydroxy-1H-thieno[3,2-d]pyrimidine-2,4-dione;
N-[3'-(3-Hydroxy-2,4-dioxo-3,4-dihydro-2H-thieno[3,2-d]pyrimidin-1 ylmethyl)-biphenyl-3-yl]-acetamide;
1-(6-Chloro-pyridin-3-ylmethyl)-3-hydroxy-1H-thieno[3,2-d]pyrimidine-2,4-dione;
3-Hydroxy-1-[6-(4-trifluoromethoxy-phenyl)-pyridin-3-ylmethyl]-1H-thieno[3,2-d]pyrimidine-2,4-dione;
3-Hydroxy-1-[6-(2-trifluoromethyl-phenyl)-pyridin-3-ylmethyl]-1H-thieno[3,2-d]pyrimidine-2,4-dione;
1-[6-(3,3-Dimethyl-but-1-enyl)-pyridin-3-ylmethyl]-3-hydroxy-1H-thieno[3,2-d]pyrimidine-2,4-dione;
3-Hydroxy-1H-benzo[4,5]thieno[3,2-d]pyrimidine-2,4-dione;
3-Hydroxy-1-(2-pyrrolidin-1-yl-ethyl)-1H-thieno[3,2-d]pyrimidine-2,4-dione;
3-Hydroxy-7-methyl-1-(4-methyl-benzyl)-1H-thieno[3,2-d]pyrimidine-2,4-dione;
3-Hydroxy-7-methyl-1-(3-methyl-benzyl)-1H-thieno[3,2-d]pyrimidine-2,4-dione;
1-(4-Bromo-benzyl)-3-hydroxy-7-methyl-1H-thieno[3,2-d]pyrimidine-2,4-dione;
1-(2'-Acetyl-biphenyl-4-ylmethyl)-3-hydroxy-7-methyl-1H-thieno[3,2-d]pyrimidine-2,4-dione;
5-(4-Bromo-phenyl)-3-hydroxy-1H-thieno[2,3-d]pyrimidine-2,4-dione;
7-Benzenesulfonyl-3-hydroxy-1H-thieno[3,2-d]pyrimidine-2,4-dione;
3-Hydroxy-7-phenyl-6-trifluoromethyl-1H-thieno[3,2-d]pyrimidine-2,4-dione;
3-Hydroxy-1-(4-methoxy-benzyl)-7-phenyl-1H-thieno[3,2-d]pyrimidine-2,4-dione;
3-Hydroxy-1-(4-methoxy-benzyl)-7-phenyl-1H-thieno[3,2-d]pyrimidine-2,4-dione;
1-(6-Chloro-pyridin-3-ylmethyl)-3-hydroxy-7-phenyl-1H-thieno[3,2-d]pyrimidine-2,4-dione;
-Hydroxy-7-phenyl-1-(3,4,5-trimethoxy-benzyl)-1H-thieno[3,2-d]pyrimidine-2,4-dione'
3-Hydroxy-7-phenyl-1-thiophen-3-ylmethyl-1H-thieno[3,2-d]pyrimidine-2,4-dione;
3-Hydroxy-1-(4-methoxy-benzyl)-1,5,6,7,8,9-hexahydro-10-thia-1,3-diaza-benzo[a]azulene-2,4-dione;
3-Hydroxy-1-thiophen-3-ylmethyl-1,5,6,7,8,9-hexahydro-10-thia-1,3-diaza-benzo[a]azulene-2,4-dione;
1-(6-Chloro-pyridin-3-ylmethyl)-3-hydroxy-1,5,6,7,8,9-hexahydro-10-thia-1,3-diaza-benzo[a]azulene-2,4-dione;
3-Hydroxy-1-methyl-1,5,6,7,8,9-hexahydro-10-thia-1,3-diaza-benzo[a]azulene-2,4-dione;
6-tert-Butyl-3-hydroxy-1-(3-methoxy-benzyl)-1H-thieno[3,2-d]pyrimidine-2,4-dione;
6-tert-Butyl-3-hydroxy-1-naphthalen-2-ylmethyl-1H-thieno[3,2-d]pyrimidine-2,4-dione;
6-tert-Butyl-3-hydroxy-1-thiophen-3-ylmethyl-1H-thieno[3,2-d]pyrimidine-2,4-dione;
6-tert-Butyl-3-hydroxy-1H-thieno[3,2-d]pyrimidine-2,4-dione;
5-[6-(4-Chloro-phenyl)-3-hydroxy-2,4-dioxo-3,4-dihydro-2H-thieno[3,2-d]pyrimidin-1-ylmethyl]-furan-2-carboxylic acid methyl ester;
3-Hydroxy-1-methyl-1H-benzo[4,5]thieno[3,2-d]pyrimidine-2,4-dione;
1-Benzyl-3-hydroxy-1H-benzo[4,5]thieno[3,2-d]pyrimidine-2,4-dione;
3-Hydroxy-1-(1-phenyl-ethyl)-1H-benzo[4,5]thieno[3,2-d]pyrimidine-2,4-dione;
1-(4-tert-Butyl-benzyl)-3-hydroxy-1H-benzo[4,5]thieno[3,2-d]pyrimidine-2,4-dione;
3-Hydroxy-1-propyl-1H-benzo[4,5]thieno[3,2-d]pyrimidine-2,4-dione and 3-Hydroxy-2-propoxy-3H-benzo[4,5]thieno[3,2-d]pyrimidin-4-one;
1-Butyl-3-hydroxy-1H-benzo[4,5]thieno[3,2-d]pyrimidine-2,4-dione and 2-Butoxy-3-hydroxy-3H-benzo[4,5]thieno[3,2-d]pyrimidin-4-one;
1-(3-Bromo-benzyl)-3-hydroxy-1H-benzo[4,5]thieno[3,2-d]pyrimidine-2,4-dione;
1-Biphenyl-2-ylmethyl-3-hydroxy-1H-benzo[4,5]thieno[3,2-d]pyrimidine-2,4-dione;
5-(3-Hydroxy-2,4-dioxo-3,4-dihydro-2H-benzo[4,5]thieno[3,2-d]pyrimidin-1-ylmethyl)-furan-2-carboxylic acid methyl ester;

3-Hydroxy-1-phenethyl-1H-benzo[4,5]thieno[3,2-d]pyrimidine-2,4-dione;
3-Hydroxy-1-(3-phenyl-allyl)-1H-benzo[4,5]thieno[3,2-d]pyrimidine-2,4-dione;
3-Hydroxy-1-pyridin-2-ylmethyl-1H-benzo[4,5]thieno[3,2-d]pyrimidine-2,4-dione;
1-(4-Bromo-benzyl)-3-hydroxy-1H-benzo[4,5]thieno[3,2-d]pyrimidine-2,4-dione;
1-(2-Bromo-benzyl)-3-hydroxy-1H-benzo[4,5]thieno[3,2-d]pyrimidine-2,4-dione;
1-Biphenyl-3-ylmethyl-3-hydroxy-1H-benzo[4,5]thieno[3,2-d]pyrimidine-2,4-dione;
1-(4'-Acetyl-biphenyl-4-ylmethyl)-3-hydroxy-1H-benzo[4,5]thieno[3,2-d]pyrimidine-2,4-dione;
3-Hydroxy-8-nitro-1H-benzo[4,5]thieno[3,2-d]pyrimidine-2,4-dione;
1-Benzyl-3-hydroxy-8-nitro-1H-benzo[4,5]thieno[3,2-d]pyrimidine-2,4-dione;
1-Biphenyl-2-ylmethyl-3-hydroxy-8-nitro-1H-benzo[4,5]thieno[3,2-d]pyrimidine-2,4-dione;
3-Hydroxy-7-(3-methoxy-phenyl)-1H-furo[3,2-d]pyrimidine-2,4-dione;
7-Biphenyl-4-yl-3-hydroxy-1H-furo[3,2-d]pyrimidine-2,4-dione;
7-Biphenyl-4-yl-3-hydroxy-1H-furo[3,2-d]pyrimidine-2,4-dione;
1-Benzyl-7-(3-bromo-phenyl)-3-hydroxy-1H-furo[3,2-d]pyrimidine-2,4-dione;
1-Benzyl-7-(3-bromo-phenyl)-3-hydroxy-1H-furo[3,2-d]pyrimidine-2,4-dione;
3-Hydroxy-1-(4-methoxy-benzyl)-7-(3-methoxy-phenyl)-1H-furo[3,2-d]pyrimidine-2,4-dione;
7-Benzyl-3-hydroxy-1H-furo[3,2-d]pyrimidine-2,4-dione;
3-Hydroxy-1H-benzo[4,5]furo[3,2-d]pyrimidine-2,4-dione;
3-Hydroxy-1-(4-methoxy-benzyl)-1H-benzo[4,5]furo[3,2-d]pyrimidine-2,4-dione;
3-Hydroxy-1-(2-methyl-thiazol-4-ylmethyl)-1H-benzo[4,5]furo[3,2-d]pyrimidine-2,4-dione;
3-Hydroxy-1-(2-methyl-thiazol-4-ylmethyl)-1H-benzo[4,5]furo[3,2-d]pyrimidine-2,4-dione;
1-Biphenyl-2-ylmethyl-3-hydroxy-1H-benzo[4,5]furo[3,2-d]pyrimidine-2,4-dione;
3-Hydroxy-1-prop-2-ynyl-1H-benzo[4,5]furo[3,2-d]pyrimidine-2,4-dione;
1-Ally-3-hydroxy-1H-benzo[4,5]furo[3,2-d]pyrimidine-2,4-dione;
3-Hydroxy-1-(1-phenyl-ethyl)-1H-benzo[4,5]furo[3,2-d]pyrimidine-2,4-dione;
3-Hydroxy-1-(3-phenyl-allyl)-1H-benzo[4,5]furo[3,2-d]pyrimidine-2,4-dione;
1-(2-Bromo-benzyl)-3-hydroxy-1H-benzo[4,5]furo[3,2-d]pyrimidine-2,4-dione;
1-(3-Bromo-benzyl)-3-hydroxy-1H-benzo[4,5]furo[3,2-d]pyrimidine-2,4-dione;
1-(4-Bromo-benzyl)-3-hydroxy-1H-benzo[4,5]furo[3,2-d]pyrimidine-2,4-dione;
1-(2,5-Difluorobiphenyl)-2-ylmethyl-3-hydroxy-1H-benzo[4,5]furo[3,2-d]pyrimidine-2,4-dione;
1-(3-Benzo[1,3]dioxol-5-yl-benzyl)-3-hydroxy-1H-benzo[4,5]furo[3,2-d]pyrimidine-2,4-dione;
4'-(3-Hydroxy-2,4-dioxo-3,4-dihydro-2H-benzo[4,5]furo[3,2-d]pyrimidin-1-ylmethyl)-biphenyl-3-carboxylic acid amide;
7-Diethylamino-3-hydroxy-1H-benzo[4,5]furo[3,2-d]pyrimidine-2,4-dione; and
1-Benzyl-7-diethylamino-3-hydroxy-1H-benzo[4,5]furo[3,2-d]pyrimidine-2,4-dione.

Certain compounds of the invention may exist in different isomeric (e.g. enantiomers and diastereoisomers) forms. The invention contemplates all such isomers both in pure form and in a mixture, including racemic mixtures. Enol forms are also included.

The compounds of the invention can exist in unsolvated as well as solvated forms, including hydrated forms, e.g., hemihydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous solutions of hydroxide, potassium carbonate, ammonia, or sodium bicarbonate. The free base forms differ from their respective salt forms in certain physical properties, such as solubility in polar solvents, but the acid salts are equivalent to their respective free base forms for purposes of the invention. (See, for example S. M. Berge, et al., "Pharmaceutical Salts," *J. Pharm. Sci.*, 66: 1-19 (1977) which is incorporated herein by reference.

As throughout this specification and appended claims, the following terms have the meanings ascribed to them:

The term "alkyl" as used herein refers to straight or branched chain radicals derived from saturated hydrocarbons by the removal of one hydrogen atom. Representative examples of alkyl groups include methyl, ethyl, n-propyl, iso-propyl, n-butyl, sec-butyl, iso-butyl, tert-butyl, and the like.

The term "cycloalkyl" as used herein refers to an aliphatic ring system having 3 to 8 carbon atoms and 1 to 3 rings, including, but not limited to cyclopropyl, cyclopentyl, and cyclohexyl, among others. Cycloalkyl groups can be unsubstituted or substituted with one, two or three substituents independently selected from lower alkyl, haloalkyl, alkoxy, thioalkoxy, amino, alkylamino, dialkylamino, hydroxyl, halo, mercapto, nitro, carboxaldehyde, carboxy, alkoxycarbonyl and carbodimide.

"Cycloalkyl" includes cis or trans forms. Furthermore, the substituents may either be in endo or exo positions in the bridged bicyclic systems.

The term "aryl" or "aromatic" as used herein alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group containing at least one endocyclic N, O or S atom such as furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxazinyl, pyrazolo[1,5-c]triazinyl and the like. "Aralkyl" and "alkylaryl" employ the term "alkyl" as defined above. Rings may be multiply substituted.

The term "heteroatom" as used herein refers to at least one N, O or S atom.

As used herein, the term "composition" is intended to encompass a product comprising the specified ingredients in the specified amounts, as well as any product which results, directly or indirectly, from a combination of the specified ingredients in the specified amounts.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isothionate), lactate, maleate, methanesulfonate, nicotinate, 2-naphthalenesulfonate, oxalate, palmitate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety or the hydroxyimide moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

The following abbreviations are used herein:

DMB=2,4-Dimethoxybenzyl;

TPPTS=3,3',3''-Phosphinidynetris(benzenesulfonic acid) trisodium salt;

CDI=Carbonyl diimidazole; and

EDC=1-(3-Diethylaminopropyl)-3-ethylcarbodiimide hydrochloride.

The following general synthetic schemes and procedures were utilized to prepare the compounds of the examples:

General Synthetic Schemes:

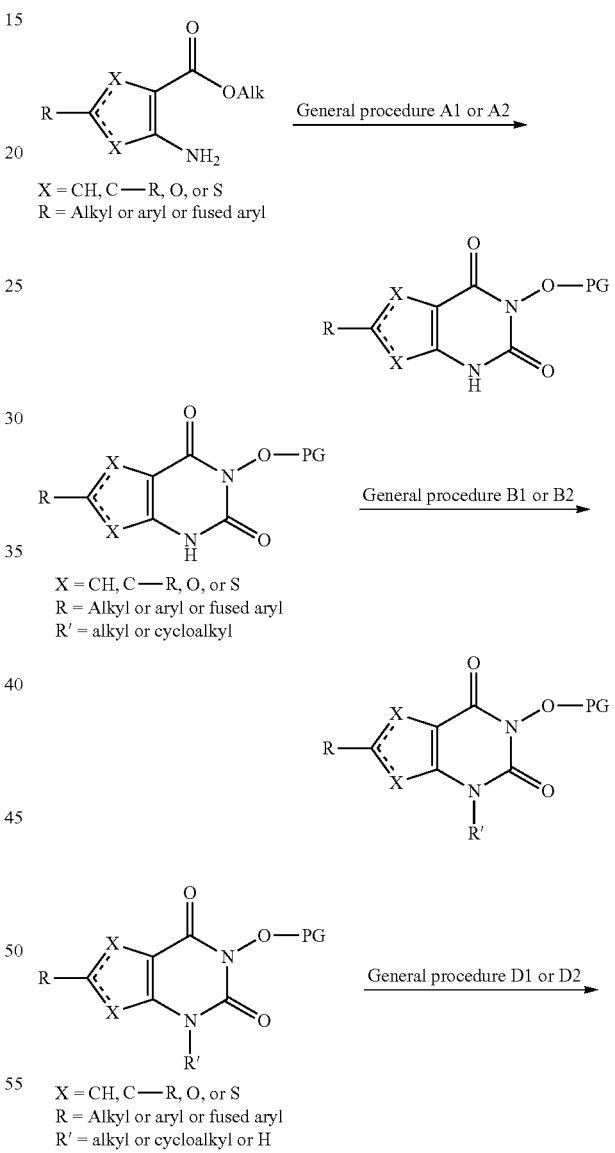

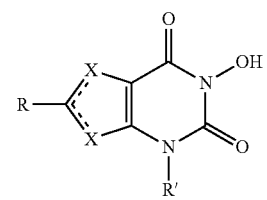

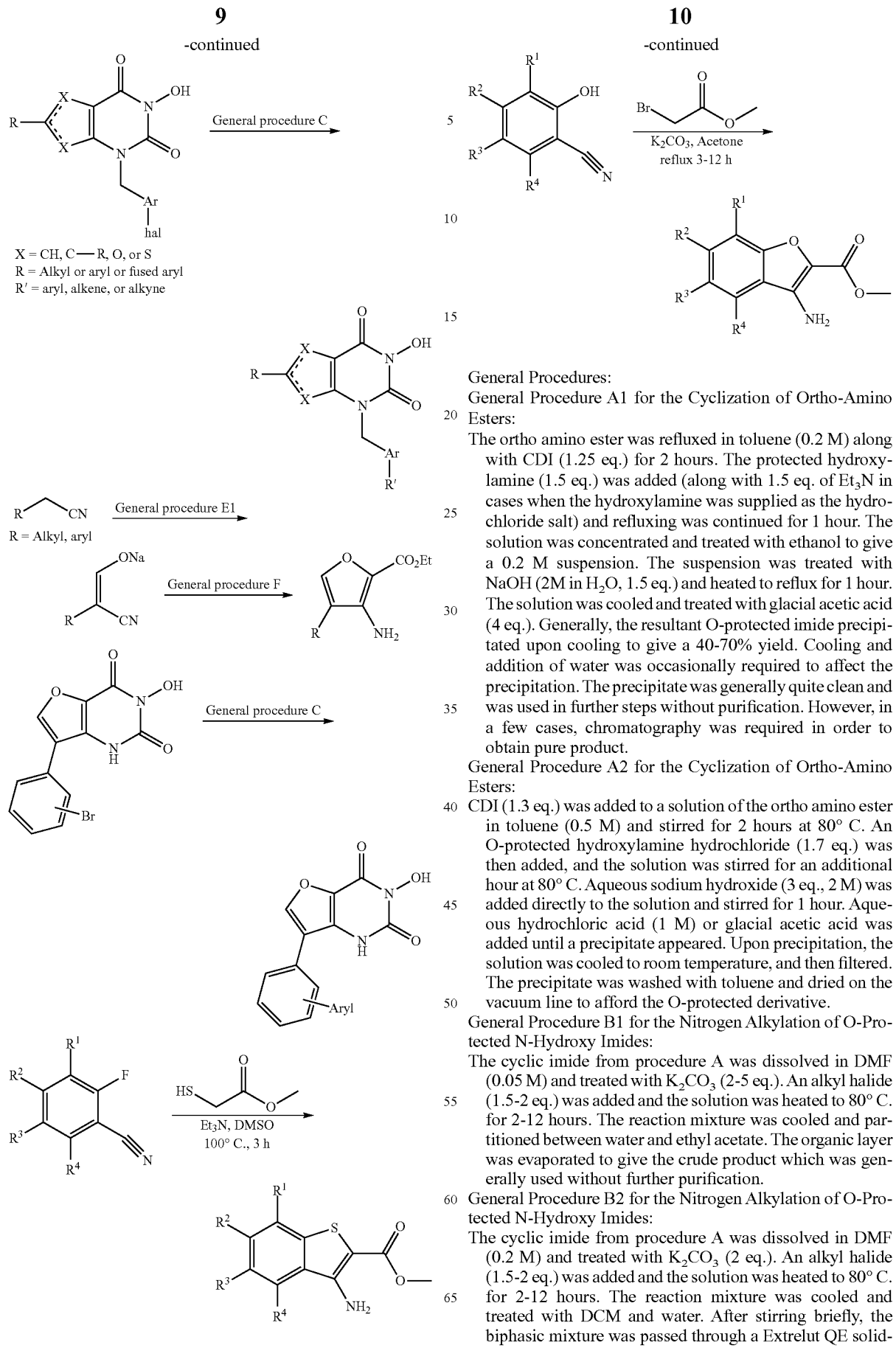

General Procedures:

General Procedure A1 for the Cyclization of Ortho-Amino Esters:

The ortho amino ester was refluxed in toluene (0.2 M) along with CDI (1.25 eq.) for 2 hours. The protected hydroxylamine (1.5 eq.) was added (along with 1.5 eq. of Et$_3$N in cases when the hydroxylamine was supplied as the hydrochloride salt) and refluxing was continued for 1 hour. The solution was concentrated and treated with ethanol to give a 0.2 M suspension. The suspension was treated with NaOH (2M in H$_2$O, 1.5 eq.) and heated to reflux for 1 hour. The solution was cooled and treated with glacial acetic acid (4 eq.). Generally, the resultant O-protected imide precipitated upon cooling to give a 40-70% yield. Cooling and addition of water was occasionally required to affect the precipitation. The precipitate was generally quite clean and was used in further steps without purification. However, in a few cases, chromatography was required in order to obtain pure product.

General Procedure A2 for the Cyclization of Ortho-Amino Esters:

CDI (1.3 eq.) was added to a solution of the ortho amino ester in toluene (0.5 M) and stirred for 2 hours at 80° C. An O-protected hydroxylamine hydrochloride (1.7 eq.) was then added, and the solution was stirred for an additional hour at 80° C. Aqueous sodium hydroxide (3 eq., 2 M) was added directly to the solution and stirred for 1 hour. Aqueous hydrochloric acid (1 M) or glacial acetic acid was added until a precipitate appeared. Upon precipitation, the solution was cooled to room temperature, and then filtered. The precipitate was washed with toluene and dried on the vacuum line to afford the O-protected derivative.

General Procedure B1 for the Nitrogen Alkylation of O-Protected N-Hydroxy Imides:

The cyclic imide from procedure A was dissolved in DMF (0.05 M) and treated with K$_2$CO$_3$ (2-5 eq.). An alkyl halide (1.5-2 eq.) was added and the solution was heated to 80° C. for 2-12 hours. The reaction mixture was cooled and partitioned between water and ethyl acetate. The organic layer was evaporated to give the crude product which was generally used without further purification.

General Procedure B2 for the Nitrogen Alkylation of O-Protected N-Hydroxy Imides:

The cyclic imide from procedure A was dissolved in DMF (0.2 M) and treated with K$_2$CO$_3$ (2 eq.). An alkyl halide (1.5-2 eq.) was added and the solution was heated to 80° C. for 2-12 hours. The reaction mixture was cooled and treated with DCM and water. After stirring briefly, the biphasic mixture was passed through a Extrelut QE solid-phase extraction tube packed with dry celite. The packed bed was eluted once with DCM and the resultant organic eluent was evaporated to give the crude product which was generally used without further purification.

General Procedure C for Palladium Catalyzed Coupling of Boronic Acids and Alkynes to Cyclic Imides Containing Aryl Halides:

The aryl halide was treated with 1:1 $H_2O/CH_3CN$ to give a 0.1-0.2 M suspension. The boronic acid, boronic ester, or alkyne (1.5 eq.) was added followed by $Pd(OAc)_2$ (0.1 eq.), TPPTS (0.3 eq.), and aqueous $Na_2CO_3$ (5 eq., 2M). The resulting suspension was stirred in a sealed vial at 85° C. overnight. The reaction mixture was then filtered through a short plug of silica gel which was then washed with ethyl acetate. The combined eluents were acidified with glacial acetic acid, concentrated, and redissolved in DMF. The crude product was purified by mass-triggered preparative HPLC as described in the general analytical methods above.

General Procedure D1 for the Deprotection of the O-2,4-Dimethoxy Benzyl Protecting Group:

The O-2,4-dimethoxy benzyl protected N-hydroxy imide was treated with 20% TFA in DCM to give a ~0.5 M solution. The deep red solution was stirred for 1.5 hours and then concentrated to dryness. DMF or MeOH was added (~1 mL/10 mg of starting material) and the solution was sonicated and then filtered through a 0.45 μm glass fiber filter. The filtrate was evaporated to give the desired product. In most cases, the resultant crude product was purified by mass triggered preparative HPLC.

General Procedure D2 for the Deprotection of the O-Allyl Protecting Group:

The allyl protected N-hydroxy imide was treated with 9:1 $CH_3CN/H_2O$ to give a 0.1 M suspension. $Pd(OAc)_2$ (0.05 eq.) and TPPTS (0.10 eq.) were added followed by $Et_2N$ (5-10 eq). The resulting solution was stirred at room temperature for 1 hour. The reaction mixture was filtered through a short plug of silica gel which was then washed with ethyl acetate. The combined eluents were concentrated and redissolved in DMF. The crude product was purified by mass-triggered preparative FPLC as described in the general analytical methods above.

General Procedure E1 for Hydroxyacrylonitrile Synthesis:

Acetonitrile was added to a solution of ethyl formate (1.1 eq.) and sodium methoxide (1.1 eq.) in MeOH (1 M). The mixture was stirred for 2 hours at reflux. The resulting precipitate was filtered, washed with ether, and dried on the vacuum line to afford the desired hydroxyacrylonitrile.
adapted from: Liskowski, V.; Vu, D. N.; Feng, X.; Rault, S. *Synthesis* 2002, 6, 753-756.

General Procedure E2 for Hydroxyacrylonitrile Synthesis:

Acetonitrile was added to a stirred solution of sodium hydride (3 eq., 60% dispersion in mineral oil) in THF (0.2 M) at 0° C. Ethyl formate (3 eq.) was added and the solution was stirred overnight at room temperature. Hexanes were added and the resulting precipitate was filtered, washed with hexanes, and dried on the vacuum line to afford the desired hydroxyacrylonitrile.
adapted from: Morris, P. E. Jr.; Elliott, A. J.; Montgomery, J. A. *J. Heterocyclic Chem.* 1999, 36, 423-427.

General Procedure F for Furan Amino Ester Synthesis

Diethyl chloromalonate (1.0 eq.) was added to a stirred solution of hydroxyacrylonitrile in DMF (1.0 M). The reaction mixture was stirred for 5 hours at room temperature and the solvent was removed. The resulting oil was dissolved in ethanol, DBN (1.0 eq.) was added, and the reaction mixture was stirred at reflux overnight. The solution was concentrated. The crude product was dissolved in ethyl acetate, washed with water, and reconcentrated. The crude product was then purified by silica gel chromoatography (ethyl acetate/hexanes; ½; v/v) to afford the desired furan amino ester.
adapted from: Liskowski, V.; Vu, D. N.; Feng, X.; Rault, S. *Synthesis* 2002, 6, 753-756.

The following general analytical conditions were utilized in the examples.

General Analytical Conditions:

HPLC analysis and purification was performed using a Waters 2525 binary gradient pump, Waters 2767 sample manager, waters 2487 UV detector (220 and 254 nM), and Waters Micromass ZQ electrospray mass spec detector. The Micromass ZQ was set for both positive and negative ionization (cone voltage=25 and 50, respectively). Analytical HPLC analysis was performed as follows:

Waters XTerra MS C18 50×4.6 mm 3.5 μm column

Mobile Phase: 10 mM Ammonium Acetate buffer at pH 5.75 and Acetonitrile

Acetonitrile: 10 to 75% at 3.5 minutes, 75 to 99% at 3.9 minutes, 99% hold to 4.2 minutes, 99 to 10% at 4.5 minutes, re-equilibrate.

Preparative HPLC was Performed as Follows:

Waters XTerra Prep MS C18 50×19 mm 5 μm column

Mobile Phase: 10 mM Ammonium Acetate buffer at pH 5.75 and Acetonitrile

Acetonitrile: 10 to 99% at 8 minutes, 99% hold to 9 minutes, 99 to 10% at 9.5 minutes, re-equilibrate NMR analysis was performed using a Bruker BioSpin UltraSheild NMR (300 MHz)

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Ophthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; 0 absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppositorywax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

Compounds of the present invention that are formed by in vivo conversion of a different compound that was administered to a mammal are intended to be included within the scope of the present invention.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The invention may be illustrated by the following representative examples.

EXAMPLE 1

3-Hydroxy-1H-thieno[2,3-d]pyrimidine-2,4-dione

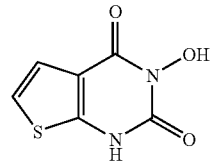

2-Amino-thiophene-3-carboxylic acid ethyl ester was transformed to the O-protected intermediate 3-(2,4-Dimethoxy-benzyloxy)-1H-thieno[2,3-d]pyrimidine-2,4-dione using general procedure A1. Deprotection of this intermediate using general procedure D1 gave the title compound which was purified by mass triggered preparative HPLC. $^1$H NMR (DMSO-$d_6$) δ 10.39 (bs, 1H), 7.16 (d, 1H, J=5.7 Hz), 7.12 (d, 1H, J=5.7 Hz); Electrospray MS: 183 (M–H); retention time: 1.25 min.

EXAMPLE 2

3-Hydroxy-1,5,6,7,8,9-hexahydro-10-thia-1,3-diazabenzo[a]azulene-2,4-dione

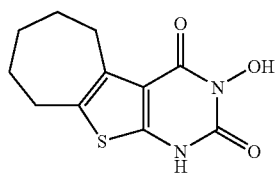

2-Amino-5,6,7,8-tetrahydro-4H-cyclohepta[b]thiophene-3-carboxylic acid ethyl ester was transformed to the corresponding DMB protected intermediate via general procedure A1. The intermediate was deprotected with TFA (general procedure D1) to give the title compound which was purified by mass triggered preparative HPLC. $^1$H NMR (DMSO-d$_6$) δ 10.22 (bs, 1H), 3.14-3.10 (m, 2H), 2.72-2.66 (m, 2H), 1.82-1.71 (m, 2H), 1.61-1.52 (m, 4H); Electrospray MS: 351 (M−H); retention time: 2.09 min.

EXAMPLE 3

1-Benzyl-3-hydroxy-5-methyl-1H-thieno[2,3-d]pyrimidine-2,4-dione

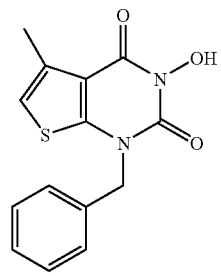

2-Amino-4-methyl-thiophene-3-carboxylic acid ethyl ester was converted to the DMB protected intermediate via general procedure A1. The intermediate was alkylated with benzyl bromide via general procedure B1. The crude product was deprotected according to general procedure D1. The desired product was purified by mass triggered preparative HPLC. $^1$H NMR (DMSO-d$_6$) δ 10.71 (bs, 1H), 7.46-7.32 (m, 5H), 6.87 (d, 1H, J=1.2 Hz), 5.21 (s, 2H), 2.43 (d, 3H, J=0.9 Hz); Electrospray MS: 289 (M+H); retention time: 2.37 min.

EXAMPLE 4

3-Hydroxy-1-(7-methoxy-benzo[1,3]dioxol-5-ylmethyl)-5-methyl-1H-thieno[2,3-d]pyrimidine-2,4-dione

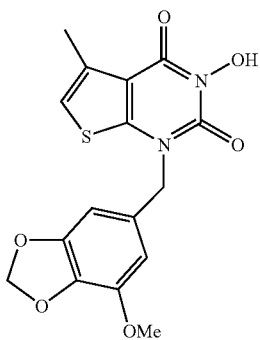

2-Amino-4-methyl-thiophene-3-carboxylic acid ethyl ester was converted to the DMB protected intermediate via general procedure A1. The intermediate was alkylated with 6-chloromethyl-4-methoxy-benzo[1,3]dioxole via general procedure B1. The crude product was deprotected according to general procedure D1. The desired product was purified by mass triggered preparative HPLC. $^1$H NMR (DMSO-d$_6$) δ 10.61 (bs, 1H), 6.82 (d, 1H, J=1.2 Hz), 6.68 (d, 1H, J=0.9 Hz), 6.54 (d, 1H, J=0.9 Hz), 5.97 (s, 2H), 5.05 (s, 2H), 3.80 (s, 3H), 2.36 (d, 3H, J=0.9 Hz); Electrospray MS: 363 (M+H); retention time: 2.37 min.

EXAMPLE 5

3-Hydroxy-5-methyl-1-(2,4,5-trimethoxy-benzyl)-1H-thieno[2,3-d]pyrimidine-2,4-dione

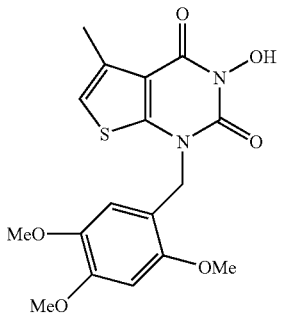

2-Amino-4-methyl-thiophene-3-carboxylic acid ethyl ester was converted to the DMB protected intermediate via general procedure A1. The intermediate was alkylated with 1-chloromethyl-2,4,5-trimethoxy-benzene via general procedure B1. The crude product was deprotected according to general procedure D1. The desired product was purified by mass triggered preparative HPLC. $^1$H NMR (DMSO-d$_6$) δ 10.6 (bs, 1H), 6.78 (s, 1H), 6.73 (s, 1H), 6.71 (s, 1H), 5.03 (s, 2H), 3.80 (s, 3H), 3.78 (s, 3H), 3.60 (s, 3H), 2.36 (s, 3H); Electrospray MS: 379 (M+H); retention time: 2.3 min.

EXAMPLE 6

1-(6-Chloro-pyridin-3-ylmethyl)-3-hydroxy-5-methyl-1H-thieno[2,3-d]pyrimidine-2,4-dione

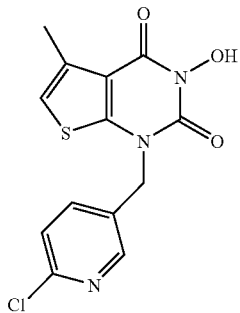

2-Amino-4-methyl-thiophene-3-carboxylic acid ethyl ester was converted to the DMB protected intermediate via general procedure A1. The intermediate was alkylated with 2-chloro-5-chloromethyl-pyridine via general procedure B1. The crude product was deprotected according to general procedure D1. The desired product was purified by mass triggered preparative HPLC. $^1$H NMR (DMSO-d$_6$) δ 10.65 (bs, 1H), 8.47 (d, 1H, J=2.7, 8.4 Hz), 7.52 (d, 1H, J=8.4 Hz), 6.84

(s, 1H), 5.20 (s, 2H), 2.37 (s, 3H); Electrospray MS: 324 (M+H); retention time: 2.07 min.

EXAMPLE 7

3-Hydroxy-5-methyl-1-quinolin-2-ylmethyl-1H-thieno[2,3-d]pyrimidine-2,4-dione

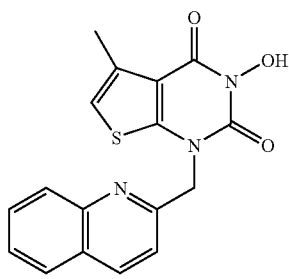

2-Amino-4-methyl-thiophene-3-carboxylic acid ethyl ester was converted to the DMB protected intermediate via general procedure A1. The intermediate was alkylated with 2-chloromethyl-quinoline via general procedure B1. The crude product was deprotected according to general procedure HPLC. $^1$H NMR (DMSO-d$_6$) δ 10.69 (bs, 1H), 8.38 (d, 1H, J=8.4 Hz), 7.97 (d, 1H, J=7.8 Hz), 7.87 (d, 1H, J=8.4 Hz), 7.73 (t, 1H, J=7.2 Hz), 7.59 (t, 1H, J=7.2 Hz), 7.52 (d, 1H, J=8.4 Hz), 6.77 (s, 1H), 5.44 (s, 2H), 2.39 (s, 3H); Electrospray MS: 340 (M+H); retention time: 2.37 min.

EXAMPLE 8

3-Hydroxy-5-methyl-1-(2-thiophen-2-yl-thiazol-4-ylmethyl)-1H-thieno[2,3-d]pyrimidine-2,4-dione

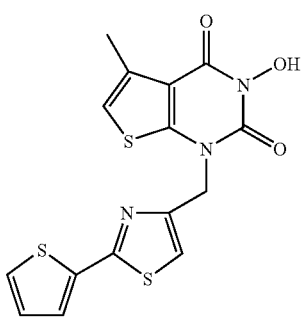

2-Amino-4-methyl-thiophene-3-carboxylic acid ethyl ester was converted to the DMB protected intermediate via general procedure A1. The intermediate was alkylated with 4-chloromethyl-2-thiophen-2-yl-thiazole via general procedure B1. The crude product was deprotected according to general procedure D1. The desired product was purified by mass triggered preparative HPLC. $^1$H NMR (DMSO-d$_6$) δ 10.64 (bs, 1H), 7.70 (dd, 1H, J=0.9, 5.1 Hz), 7.63 (dd, 1H, J=0.9, 3.6 Hz), 7.59 (s, 1H), 7.14 (dd, 1H, J=3.6, 5.1 Hz), 6.84 (d, 1H, J=1.2 Hz), 5.24 (s, 2H), 2.49 (s, 3H); Electrospray MS: 378 (M+H); retention time: 2.65 min.

EXAMPLE 9

3-Hydroxy-1-naphthalen-2-ylmethyl-1H-thieno[2,3-d]pyrimidine-2,4-dione

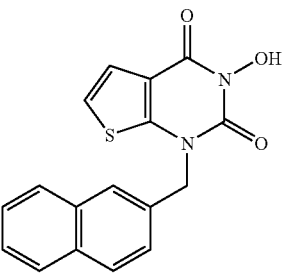

2-Amino-thiophene-3-carboxylic acid ethyl ester was converted to the DMB protected intermediate via general procedure A1. The intermediate was alkylated with 2-Bromomethyl-naphthalene via general procedure B1. The crude product was deprotected according to general procedure D1. The desired product was purified by mass triggered preparative HPLC. $^1$H NMR (DMSO-d$_6$) δ 10.85 (bs, 1H), 8.04-7.94 (m, 4H), 7.60 (d, 1H, J=9 Hz), 7.59 (d, 1H, J=3 Hz), 7.55 (dd, 1H, J=1.5, 8.4 Hz), 7.36 (d, 1H, J=5.7 Hz), 7.27 (d, 1H, J=5.7 Hz), 5.45 (s, 2H); Electrospray MS: 325 (M+H); retention time: 2.57 min.

EXAMPLE 10

3-Hydroxy-6-phenyl-1H-thieno[3,2-d]pyrimidine-2,4-dione

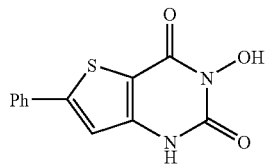

3-Amino-5-phenyl-thiophene-2-carboxylic acid ethyl ester was converted to 3-(2,4-Dimethoxy-benzyloxy)-6-phenyl-1H-thieno[3,2-d]pyrimidine-2,4-dione via general procedure A1. The intermediate was deprotected via general procedure D1 to give the title compound. $^1$H NMR (DMSO-d$_6$) δ 10.50 (bs, 1H), 9.04 (s, 1H), 7.76-7.45 (m, 5H); Electrospray MS: 259 (M−H); retention time: 1.27 min.

EXAMPLE 11

3-Hydroxy-6-phenyl-1-(tetrahydro-furan-2-ylmethyl)-1H-thieno[3,2-d]pyrimidine-2,4-dione

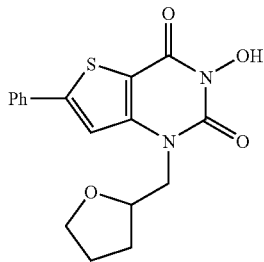

3-(2,4-dimethoxy-benzyloxy)-6-phenyl-1H-thieno[3,2-d]pyrimidine-2,4-dione (from previous example) was alkylated with 2-bromomethyl-tetrahydro-furan via general procedure B1. This crude intermediate was deprotected via general procedure D1 to give the title compound which was purified by mass-triggered preparative HPLC. $^1$H NMR (DMSO-d$_6$) δ 7.80 (d, 2H, J=8.1 Hz), 7.78 (s, 1H), 7.52-7.44 (m, 3H), 4.23-4.06 (m, 3H), 3.74 (dd, 1H, J=7.8, 13.8 Hz), 3.59 (dd, 1H, J=7.5, 13.8 Hz), 2.05-1.58 (m, 4H); Electrospray MS: 345 (M+H); retention time: 2.43 min.

EXAMPLE 12

3-Hydroxy-7-phenyl-1H-thieno[3,2-d]pyrimidine-2,4-dione

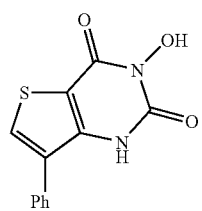

3-Amino-4-phenyl-thiophene-2-carboxylic acid ethyl ester was transformed to the corresponding DMB protected intermediate via general procedure A1. The intermediate was deprotected with TFA (general procedure D1) to give the title compound which was purified by mass triggered preparative HPLC. $^1$H NMR (DMSO-d$_6$) δ 10.71 (bs, 1H), 8.38 (d, 1H, J=7.5 Hz), 8.12 (d, 1H, J=7.8 Hz), 7.64 (dt, 1H, J=1.2, 6.9 Hz), 7.56 (dt, 1H, J=1.2, 7.8 Hz); Electrospray MS: 233 (M−H); retention time: 1.27 min.

EXAMPLE 13

1-(3-Bromo-benzyl)-3-hydroxy-1H-thieno[3,2-d]pyrimidine-2,4-dione

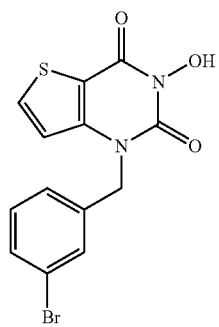

a.) 3-allyloxy-1H-thieno[3,2-d]pyrimidine-2,4-dione.

3-Amino-thiophene-2-carboxylic acid ethyl ester (2 grams, 12.7 mmol) and CDI (2.3 g, 14 mmol) were refluxed 20 mL in toluene overnight. O-Allyl hydroxylamine hydrochloride (1.7 g, 15.5 mmol) and Et$_3$N (2.2 mL, 15.5 mmol) were added and solution was again brought to reflux for 3 hours. The solution was cooled, concentrated, and redissolved in 25 mL hot ethanol. NaOH was added (16 mL of a 2 M aq. solution) and the mixture was heated to reflux for 1 hour. The reaction mixture was acidified with 1 mL of glacial acetic acid and cooled. The resultant precipitate was filtered and discarded. The filtrate was concentrated, treated with 20 mL of ethanol, sonicated briefly, and then filtered to give 1.3 grams of 3-allyloxy-1H-thieno[3,2-d]pyrimidine-2,4-dione.

b.) 1-(3-Bromo-benzyl)-3-hydroxy-1H-thieno[3,2-d]pyrimidine-2,4-dione

3-Allyloxy-1H-thieno[3,2-d]pyrimidine-2,4-dione was alkylated with 3-bromo-benzyl bromide via general procedure B1. This crude intermediate was treated with 9:1 CH$_3$CN/H$_2$O to give a 0.1 M suspension. Pd(OAc)$_2$ (0.05 eq.) and TPPTS (0.15 eq.) were added followed by Et$_2$N (5 eq). The resulting solution was stirred at room temperature for 1 hour. The solution was acidified with glacial acetic acid. The resultant white precipitate was filtered to give pure 1-(3-bromo-benzyl)-3-hydroxy-1H-thieno[3,2-d]pyrimidine-2,4-dione.

¹HNMR (DMSO-d₆) δ 10.74 (bs, 1H), 8.13 (d, 1H, J=5.1 Hz), 7.57 (s, 1H), 7.49 (ddd, 1H, J=2.4, 5.7, 8.7 Hz), 7.34-7.29 (m, 3H), 5.28 (s, 2H); Electrospray MS: 353 (M+H); retention time: 2.34 min.

EXAMPLE 14

3-Hydroxy-1-naphthalen-2-ylmethyl-1H-thieno[3,2-d]pyrimidine-2,4-dione

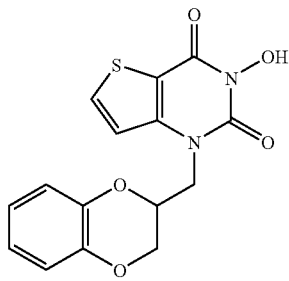

3-Allyloxy-1-(3-bromo-benzyl)-1H-thieno[3,2-d]pyrimidine-2,4-dione was alkylated with 2-bromomethyl-2,3-dihydro-benzo[1,4]dioxine via general procedure B2. The crude intermediate was deprotected via general procedure D2. The final product was purified by mass triggered preparative HPLC. Electrospray MS: 333 (M+H); retention time: 2.05 min.

EXAMPLE 15

1-(2-Chloro-benzyl)-3-hydroxy-1H-thieno[3,2-d]pyrimidine-2,4-dione

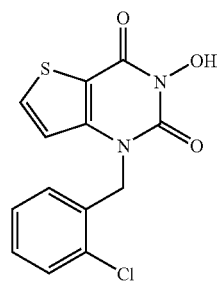

3-Allyloxy-1-(3-bromo-benzyl)-1H-thieno[3,2-d]pyrimidine-2,4-dione (from previous example) was alkylated with 1-bromomethyl-2-chloro-benzene via general procedure B2. The crude intermediate was deprotected via general procedure D2. The final product was purified by mass triggered preparative HPLC. ¹H NMR (DMSO-d₆) δ 10.65 (bs, 1H), 8.10 (d, 1H, J=5.1 Hz), 7.52 (dd, 1H, J=1.5, 7.8 Hz), 7.32 (dt, 1H, J=1.5, 7.5 Hz), 7.25 (dt, 1H, J=1.5, 7.5 Hz), 7.13 (d, 1H, J=5.4 Hz), 6.96 (dd, 1H, J=1.5, 7.5 Hz), 5.31 (s, 2H); Electrospray MS: 309 (M+H); retention time: 2.31 min.

EXAMPLE 16

3'-(3-Hydroxy-2,4-dioxo-3,4-dihydro-2H-thieno[3,2-d]pyrimidin-1-ylmethyl)-biphenyl-4-carboxylic acid amide

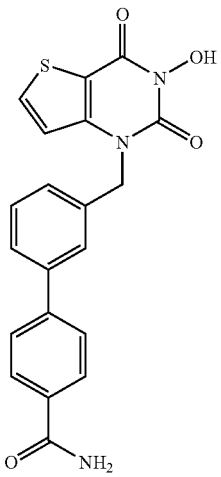

The title compound was prepared from 1-(3-Bromo-benzyl)-3-hydroxy-1H-thieno[3,2-d]pyrimidine-2,4-dione (from previous example) and 4-aminocarbonyl-phenyl boronic acid via general procedure C. The crude product was purified by mass-triggered preparative HPLC. ¹H NMR (DMSO-d₆) δ 10.87 (bs, 1H), 8.11 (d, 1H, J=5.4 Hz), 7.96 (d, 2H, J=8.4 Hz), 7.74 (s, 1H), 7.71 (d, 2H, J=7.8 Hz), 7.63 (d, 1H, J=7.8 Hz), 7.45 (t, 1H, J=7.8 Hz), 7.36 (d, 1H, J=5.4 Hz), 7.28 (d, 1H, J=7.5 Hz), 5.35 (s, 2H); Electrospray MS: 394 (M+H); retention time: 1.96 min.

EXAMPLE 17

1-(3'-Acetyl-biphenyl-3-ylmethyl)-3-hydroxy-1H-thieno[3,2-d]pyrimidine-2,4-dione

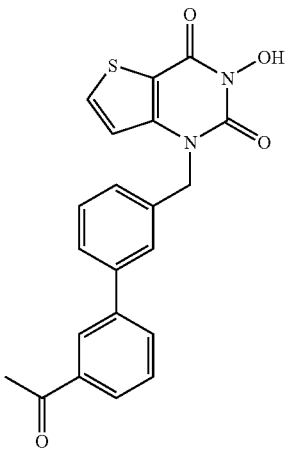

The title compound was prepared from 1-(3-Bromo-benzyl)-3-hydroxy-1H-thieno[3,2-d]pyrimidine-2,4-dione (from previous example) and 3-acetyl-phenyl boronic acid via general procedure C. The crude product was purified by mass-triggered preparative HPLC.

$^1$H NMR (DMSO-$d_6$) δ 10.74 (bs, 1H), 8.15 (s, 1H), 8.11 (d, 1H, J=5.4 Hz), 7.96 (d, 1H, J=7.8 Hz), 7.89 (d, 1H, J=7.8 Hz), 7.76 (s, 1H), 7.65 (d, 1H, J=7.8 Hz), 7.62 (t, 1H, J=7.8 Hz), 7.45 (t, 1H, J=7.8 Hz), 7.36 (d, 1H, J=5.7 Hz), 7.27 (d, 1H, J=7.5 Hz), 5.37 (s, 2H), 2.64 (s, 3H); Electrospray MS: 393 (M+H); retention time: 2.52 min.

EXAMPLE 18

N-[3'-(3-Hydroxy-2,4-dioxo-3,4-dihydro-2H-thieno[3,2-d]pyrimidin-1-ylmethyl)-biphenyl-3-yl]-acetamide

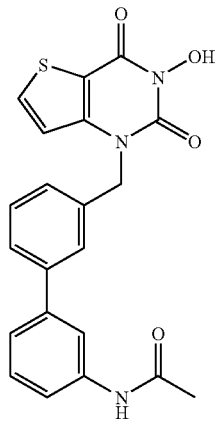

The title compound was prepared from 1-(3-Bromo-benzyl)-3-hydroxy-1H-thieno[3,2-d]pyrimidine-2,4-dione (from previous example) and 3-acetamino-phenyl boronic acid via general procedure C. The crude product was purified by mass-triggered preparative HPLC.

$^1$H NMR (DMSO-$d_6$) δ 10.90 (bs, 1H), 8.12 (d, 1H, J=5.4 Hz), 8.05 (d, 1H, J=8.1 Hz), 7.79 (d, 1H, J=8.4 Hz), 7.77 (s, 1H), 7.66 (d, 1H, J=7.8 Hz), 7.47 (t, 1H, J=7.8 Hz), 5.37 (s, 2H), 2.61 (s, 3H); Electrospray MS: 393 (M+H); retention time: 2.56 min.

EXAMPLE 19

1-(6-Chloro-pyridin-3-ylmethyl)-3-hydroxy-1H-thieno[3,2-d]pyrimidine-2,4-dione

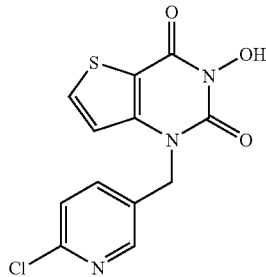

Allyloxy-1H-thieno[3,2-d]pyrimidine-2,4-dione (from previous example) was alkylated with 2-chloro-5-chloromethyl-pyridine via general procedure B1. The crude material was treated with 9:1 CH$_3$CN/H$_2$O to give a 0.1 M suspension. Pd(OAc)$_2$ (0.05 eq.) and TPPTS (0.15 eq.) were added followed by Et$_2$N (5 eq). The resulting solution was stirred at room temperature for 1 hour. The solution was acidified with glacial acetic acid. The resultant white precipitate was filtered to give pure 1-(6-chloro-pyridin-3-ylmethyl)-3-hydroxy-1H-thieno[3,2-d]pyrimidine-2,4-dione. $^1$H NMR (DMSO-$d_6$) δ 8.46 (d, 1H, J=2.4 Hz), 8.13 (d, 1H, J=5.4 Hz), 7.77 (dd, 1H, J=2.4, 8.4 Hz), 7.48 (d, 1H, J=8.4 Hz), 7.38 (d, 1H, J=5.1 Hz), 5.30 (s, 2H); Electrospray MS: 308 (M+H); retention time: 1.66 min.

EXAMPLE 20

3-Hydroxy-1-[6-(4-trifluoromethoxy-phenyl)-pyridin-3-ylmethyl]-1H-thieno[3,2-d]pyrimidine-2,4-dione

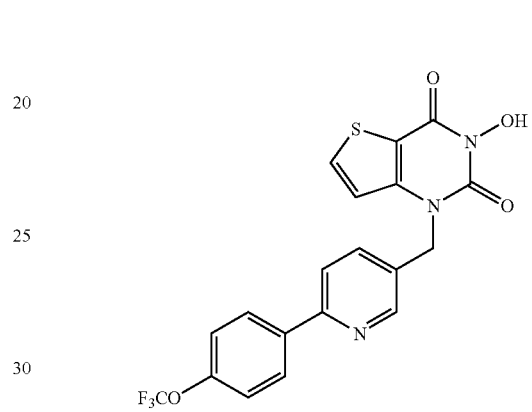

The title compound was prepared from 1-(6-chloro-pyridin-3-ylmethyl)-3-hydroxy-1H-thieno[3,2-d]pyrimidine-2,4-dione (from previous example) and 4-trifluoromethoxy phenylboronic acid via general procedure C. The crude product was purified by mass-triggered preparative HPLC. $^1$H NMR (DMSO-$d_6$) δ 10.85 (bs, 1H), 8.72 (d, 1H, J=1.8 Hz), 8.17 (d, 1H, J=8.7 Hz), 8.16 (d, 1H, J=5.5 Hz), 7.97 (d, 1H, J=8.1 Hz), 7.82 (dd-1H, J=1.8, 8.1 Hz), 7.47 (d, 2H, J=8.7 Hz), 7.45 (d, 1H, J=5.5 Hz), 5.40 (s, 2H); Electrospray MS: 436 (M+H); retention time: 2.84 min.

EXAMPLE 21

3-Hydroxy-1-[6-(2-trifluoromethyl-phenyl)-pyridin-3-ylmethyl]-1H-thieno[3,2-d]pyrimidine-2,4-dione

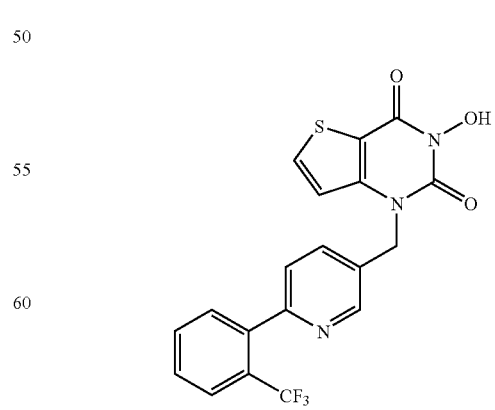

The title compound was prepared from 1-(6-chloro-pyridin-3-ylmethyl)-3-hydroxy-1H-thieno[3,2-d]pyrimidine-2, 4-dione and 2-trifluoromethyl phenylboronic acid via general procedure C. The crude product was purified by mass-triggered preparative HPLC. ¹H NMR (DMSO-d₆) δ 10.78 (bs, 1H), 8.68 (d, 1H, J=2.1 Hz), 8.18 (d, 1H, J=5.4 Hz), 7.85 (d, 1H, J=8.1 Hz), 7.80 (dd, 1H, J=2.1, 8.1 Hz), 7.75 (t, 1H, J=7.5 Hz), 7.66 (t, 1H, J=7.8 Hz), 7.56-7.46 (m, 3H), 5.39 (s, 2H); Electrospray MS: 420 (M+H); retention time; 2.44 min.

EXAMPLE 22

1-[6-(3,3-Dimethyl-but-1-enyl)-pyridin-3-ylmethyl]-3-hydroxy-1H-thieno[3,2-d]pyrimidine-2,4-dione

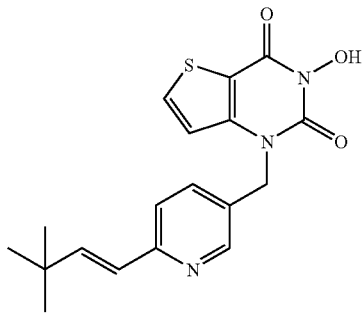

The title compound was prepared from 1-(6-chloro-pyridin-3-ylmethyl)-3-hydroxy-1H-thieno[3,2-d]pyrimidine-2,4-dione and 2-tert-butyl vinyl boronic acid via general procedure C. The crude product was purified by mass-triggered preparative HPLC. ¹H NMR (DMSO-d₆) δ 10.8 (bs, 1H), 8.53 (d, 1H, J=2.1 Hz), 8.14 (d, 1H, J=5.4 Hz), 7.62 (dd, 1H, J=2.1, 7.8 Hz), 7.38 (d, 1H, J=5.1 Hz), 7.36 (d, 1H, J=7.8 Hz), 6.78 (d, 1H, J=16.2 Hz), 6.35 (d, 1H, J=16.2 Hz), 5.29 (s, 2H), 1.09 (s, 9H); Electrospray MS: 358 (M+H); retention time: 2.62 min.

EXAMPLE 23

3-Hydroxy-1H-benzo[4,5]thieno[3,2-d]pyrimidine-2,4-dione

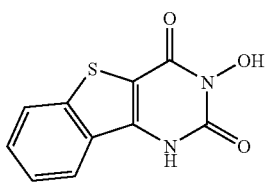

The title compound was transformed to the O-protected using general procedure A1. Deprotection of this intermediate using general procedure D1 gave the title compound which was purified by mass triggered preparative HPLC. ¹H NMR (DMSO-d₆) δ 10.71 (bs, 1H), 8.38 (d, 1H, J=7.5 Hz), 8.12 (d, 1H, J=7.8 Hz), 7.64 (dt, 1H, J=1.2, 6.9 Hz), 7.56 (dt, 1H, J=1.2, 7.8 Hz); Electrospray MS: 233 (M–H); retention time: 1.27 min.

EXAMPLE 24

3-Hydroxy-1-(2-pyrrolidin-1-yl-ethyl)-1H-thieno[3,2-d]pyrimidine-2,4-dione

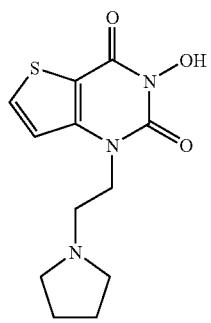

3-Allyloxy-1H-thieno[3,2-d]pyrimidine-2,4-dione (from previous example) was alkylated with 2-bromoethanol via general procedure B1. The intermediate alcohol was treated with tosyl chloride (3 eq) in pyridine (0.2 M). After 4 hours, the reaction mixture was partitioned between EtOAc and water. The organic layer was dried over MgSO₄ and concentrated to give toluene-4-sulfonic acid 2-(3-allyloxy-2,4-dioxo-3,4-dihydro-2H-thieno[3,2-d]pyrimidin-1-yl)-ethyl ester. This material could be used crude or could be further purified by chromatography in 1:1 EtOAc/hexanes. The tosylate was treated with pyrrolidine (1.5 eq) and Et₃N (1.5 eq) in CHCl₃. The reaction was heated to 55° C. for 2 hours. Additional pyrrolidine (2 eq) was added and the reaction was stirred overnight at 55° C. The reaction was cooled, washed with water, and concentrated. The crude intermediate was deprotected via general procedure D2 to give the title compound which was purified by mass-triggered preparative HPLC. ¹H NMR (DMSO-d₆) δ 8.14 (d, 1H, J=5.4 Hz), 7.32 (d, 1H, J=5.4 Hz), 4.14 (t, 2H, J=6.9 Hz), 3.60-3.30 (m, 4H), 2.67 (t, 2H, J=6.9 Hz), 1.69-1.60 (m, 4H); Electrospray MS: 322 (M+H); retention time: 1.24 min.

EXAMPLE 25

3-Hydroxy-7-methyl-1-(4-methyl-benzyl)-1H-thieno[3,2-d]pyrimidine-2,4-dione

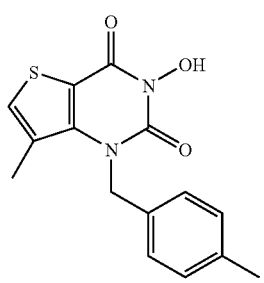

Methyl 3-amino-4-methylthiophene-2-carboxylate was converted to the title compound following general procedure A2, general procedure B2, and general procedure D2. $^1$H NMR (DMSO-d$_6$) δ 10.22 (bs, 1H), 7.74 (s, 1H), 7.17 (d, 2H), 7.00 (d, 2H), 5.4 (d, 2H), 2.27 (s, 3H), 2.21 (s, 3H); Electrospray MS: 302, obsd. 303 (M+H); retention time: 2.42 min.

EXAMPLE 26

3-Hydroxy-7-methyl-1-(3-methyl-benzyl)-1H-thieno[3,2-d]pyrimidine-2,4-dione

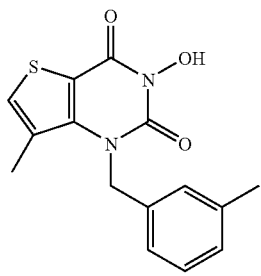

Methyl 3-amino-4-methylthiophene-2-carboxylate was converted to the title compound following general procedure A2, general procedure B2, and general procedure D2. $^1$H NMR (DMSO-d$_6$) δ 10.22 (bs, 1H), 7.75 (s, 1H), 7.28-7.68 (m, 4H), 5.41 (s, 2H), 2.28 (s, 3H), 2.21 (s, 3H); Electrospray MS: 302, obsd. 303 (M+H); retention time: 2.44 min.

EXAMPLE 27

1-(4-Bromo-benzyl)-3-hydroxy-7-methyl-1H-thieno[3,2-d]pyrimidine-2,4-dione

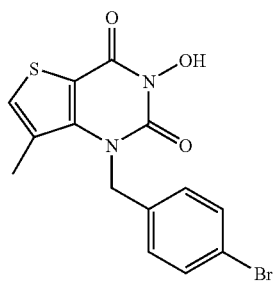

Methyl 3-amino-4-methylthiophene-2-carboxylate was converted to the title compound following general procedure A2, general procedure B2, and general procedure D2. $^1$H NMR (DMSO-d$_6$) δ 10.22 (bs, 1H), 7.76 (s, 1H), 7.54 (d, 2H), 7.12 (d, 2H), 5.4 (s, 2H), 2.18 (s, 3H); Electrospray MS: 366, obsd. 367 (M+H); retention time: 2.52 min.

EXAMPLE 28

1-(2'-Acetyl-biphenyl-4-ylmethyl)-3-hydroxy-7-methyl-1H-thieno[3,2-d]pyrimidine-2,4-dione

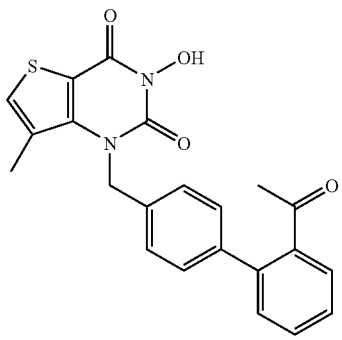

Methyl 3-amino-4-methylthiophene-2-carboxylate was converted to the title compound following general procedure A2, general procedure B2, general procedure D2, and general procedure C. $^1$HNMR (DMSO-d$_6$) δ 10.22 (bs, 1H), 7.17-7.71 (m, 9H), 5.51 (s, 2H), 2.28 (s, 3H), 2.13 (s, 3H); Electrospray MS: 406, obsd. 407 (M+H); retention time: 2.66 min.

EXAMPLE 29

5-(4-Bromo-phenyl)-3-hydroxy-1H-thieno[2,3-d]pyrimidine-2,4-dione

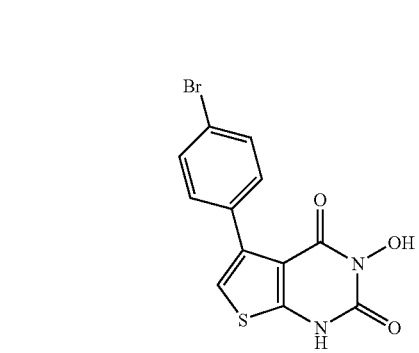

2-Amino-4-(4-bromo-phenyl)-thiophene-3-carboxylic acid ethyl ester was converted to the DMB protected intermediate via general procedure A1. Deprotection of this intermediate using general procedure D1 gave the title compound which was purified by mass triggered preparative HPLC. $^1$H NMR (DMSO-d6) δ 7.57 (d, J=8.4 Hz, 2H), 7.41 (d, J=8.4 Hz 2H), 7.01 (s, 1H); Electrospray MS: 337 (M−H); retention time: 2.26 min.

EXAMPLE 30

7-Benzenesulfonyl-3-hydroxy-1H-thieno[3,2-d]pyrimidine-2,4-dione

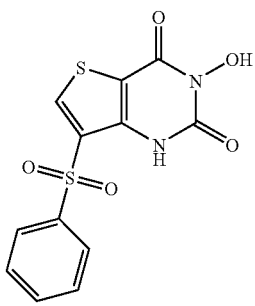

EDC (1.5 eq.) was added to a solution of 3-Amino-4-benzenesulfonyl-thiophene-2-carboxylic acid, O-(2,4-Dimethoxy-benzyl)-hydroxylamine (1 eq), and Et3N (1 eq) in methylene chloride (0.05 M) and stirred at ambient temperature overnight. The reaction was then washed with $H_2O$, dried over $MgSO_4$, and filtered. CDI was added to the reaction and stirred at ambient temperature for 2 hours. The crude product was purified by flash chromatography (1-5% EtOH in DCM). Deprotection of this intermediate using general procedure D1 gave the title compound. $^1$H NMR (DMSO-d6) δ 10.77 (bs, 1H), 9.00 (s, 1H), 8.22 (d, J=7.2 Hz, 2H), 7.77-7.62 (m, 3H); Electrospray MS: 325 (M+H); retention time: 1.6 min.

EXAMPLE 31

3-Hydroxy-7-phenyl-6-trifluoromethyl-1H-thieno[3,2-d]pyrimidine-2,4-dione

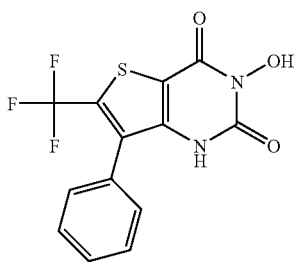

3-Amino-4-phenyl-5-trifluoromethyl-thiophene-2-carboxylic acid methyl ester was converted to the cyclic intermediate via general procedure A1. Deprotection of the intermediate using general procedure D1 gave the title compound which was purified by mass triggered preparative HPLC. $^1$H NMR (DMSO-d6) δ 10.70 (bs, 1H), 7.51-7.47 (m, 3H), 7.36-7.33 (m, 2H); Electrospray MS: 329 (M+H); retention time: 2.44 min.

EXAMPLE 32

3-Hydroxy-1-methyl-7-phenyl-1H-thieno[3,2-d]pyrimidine-2,4-dione

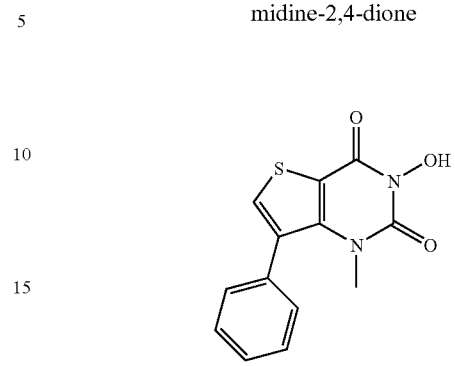

3-Amino-4-phenyl-thiophene-2-carboxylic acid methyl ester was converted to the cyclic intermediate via general procedure A1. The intermediate was alkylated with methyl iodide via general procedure B1. Deprotection of this intermediate using general procedure D1 gave the title compound which was purified by mass triggered preparative HPLC. $^1$H NMR (DMSO-d$_6$), δ 10.87 (bs, 1H), 7.96 (s, 1H), 7.45 (s, 1H), 3.01 (s, 3H); Electrospray MS: 275 (M+H); retention time: 2.17 min.

EXAMPLE 33

3-Hydroxy-1-(4-methoxy-benzyl)-7-phenyl-1H-thieno[3,2-d]pyrimidine-2,4-dione

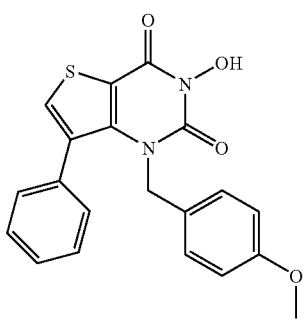

3-Amino-4-phenyl-thiophene-2-carboxylic acid methyl ester was converted to the cyclic intermediate via general procedure A1. The intermediate was alkylated with 1-chloromethyl-4-methoxy-benzene via general procedure B1. Deprotection of this intermediate using general procedure D1 gave the title compound which was purified by mass triggered preparative HPLC. $^1$H NMR (DMSO-d6), δ 10.85 (bs, 1H), 7.90 (s, 1H), 7.37 (tt, J=1.5 Hz, 7.2 Hz, 1H), 7.28 (t, J=7.5 Hz, 2H), 7.17 (d, J=6.9 Hz, 2H), 6.71 (d, J=8.7 Hz, 2H), 6.54 (d, J=8.7 Hz, 2H), 4.87 (s, 2H), 3.67 (s, 3H); Electrospray MS: 381 (M+H); retention time: 2.74 min.

EXAMPLE 34

1-(6-Chloro-pyridin-3-ylmethyl)-3-hydroxy-7-phenyl-1H-thieno[3,2-d]pyrimidine-2,4-dione

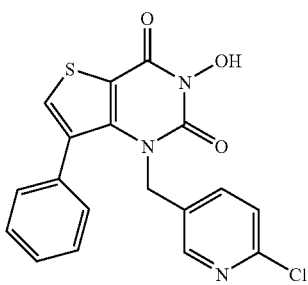

3-Amino-4-phenyl-thiophene-2-carboxylic acid methyl ester was converted to the cyclic intermediate via general procedure A1. The intermediate was alkylated with 2-chloro-5-chloromethyl-pyridine via general procedure B1. Deprotection of this intermediate using general procedure D gave the title compound which was purified by mass triggered preparative HPLC. $^1$H NMR (DMSO-d6), δ 10.61 (bs, 1H), 7.90 (s, 1H), 7.67 (d, J=2.1 Hz, 1H), 7.34 (tt, J=1.2 Hz, 7.5 Hz, 2H), 7.29 (d, J=8.1 Hz, 1H), 7.23-7.19 (m, 3H), 7.13 (d, J=6.9 Hz, 1H), 4.94 (s, 2H); Electrospray MS: 386 (M+H); retention time: 2.46 min.

EXAMPLE 35

3-Hydroxy-7-phenyl-1-(3,4,5-trimethoxy-benzyl)-1H-thieno[3,2-d]pyrimidine-2,4-dione

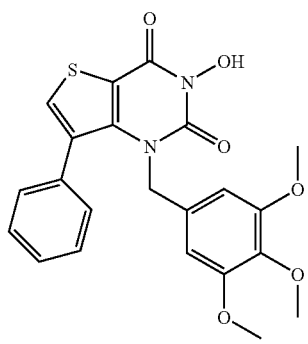

3-Amino-4-phenyl-thiophene-2-carboxylic acid methyl ester was converted to the cyclic intermediate via general procedure A1. The intermediate was alkylated with 5-chloromethyl-1,2,3-trimethoxy-benzene via general procedure B1. Deprotection of this intermediate using general procedure D gave the title compound which was purified by mass triggered preparative HPLC. $^1$H NMR (DMSO-d6), δ 10.90 (bs, 1H), 7.88 (s, 1H), 7.34 (t, J=7.2 Hz, 1H), 7.25 (t, J=7.5 Hz, 2H), 7.14 (d, J=6.9 Hz, 2H), 5.77 (s, 2H), 4.90 (s, 2H), 3.58 (s, 3H), 3.56 (s, 6H); Electrospray MS: 441(M+H); retention time: 2.47 min.

EXAMPLE 36

3-Hydroxy-7-phenyl-1-thiophen-3-ylmethyl-1H-thieno[3,2-d]pyrimidine-2,4-dione

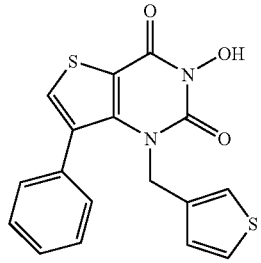

3-Amino-4-phenyl-thiophene-2-carboxylic acid methyl ester was converted to the cyclic intermediate via general procedure A1. The intermediate was alkylated with 3-chloromethyl-thiophene via general procedure B1. Deprotection of this intermediate using general procedure D gave the title compound which was purified by mass triggered preparative HPLC. $^1$HNMR (DMSO-d6) δ 10.90 (bs, 1H), 7.91 (s, 1H), 7.47-7.27 (m, 5H), 7.18 (d, J=7.2 Hz, 1H), 6.80 (s, 1H), 6.42 (d, J=4.8 Hz, 1H), 4.90 (s, 2H); Electrospray MS: 357(M+H); retention time: 2.74 min.

EXAMPLE 37

3-Hydroxy-1-(4-methoxy-benzyl)-1,5,6,7,8,9-hexahydro-10-thia-1,3-diaza-benzo[a]azulene-2,4-dione

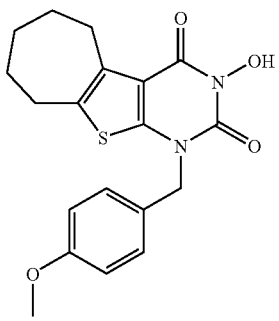

2-Amino-5,6,7,8-tetrahydro-4H-cyclohepta[b]thiophene-3-carboxylic acid ethyl ester was converted to the cyclic intermediate via general procedure A1. The intermediate was purified by chromatography (EtOAc/Hex) and then alkylated with 1-chloromethyl-4-methoxy-benzene via general procedure B1. Deprotection of this intermediate using general procedure D gave the title compound which was purified by mass triggered preparative HPLC. $^1$H NMR (CDCl$_3$), δ 7.37 (d, J=8.7 Hz, 2H), 6.86 (d, J=8.7 Hz, 2H), 5.11 (s, 2H), 3.79 (s, 3H), 3.20 (t, J=5.7 Hz, 2H), 1.86-1.82 (m, 2H), 1.69 (pent., J=5.4 Hz, 4H); Electrospray MS: 373(M+H); retention time: 3.11 min.

EXAMPLE 38

3-Hydroxy-1-thiophen-3-ylmethyl-1,5,6,7,8,9-hexahydro-10-thia-1,3-diaza-benzo[a]azulene-2,4-dione

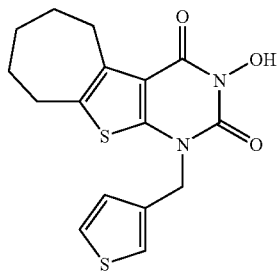

2-Amino-5,6,7,8-tetrahydro-4H-cyclohepta[b]thiophene-3-carboxylic acid ethyl ester was converted to the cyclic intermediate via general procedure A1. The intermediate was alkylated with 3-chloromethyl-thiophene via general procedure B1. Deprotection of this intermediate using general procedure D gave the title compound which was purified by mass triggered preparative HPLC. $^1$H NMR (CDCl$_3$) δ 7.40 (d, J=2.4 Hz, 1H), 7.30 (dd, J=3.0 Hz, 5.1 Hz, 1H), 7.18 (dd, J=1.2 Hz, 5.1 Hz, 1H), 5.15 (s, 2H), 3.21 (t, J=5.6 Hz, 2H), 2.75 (t, J=5.6 Hz, 2H), 1.73-1.63 (m, 4H), 1.91-1.84 (m, 2H); Electrospray MS: 349(M+H); retention time: 3.01 min.

EXAMPLE 39

1-(6-Chloro-Pyridin-3-ylmethyl)-3-hydroxy-1,5,6,7,8,9-hexahydro-10-thia-1,3-diaza-benzo[a]azulene-2,4-dione

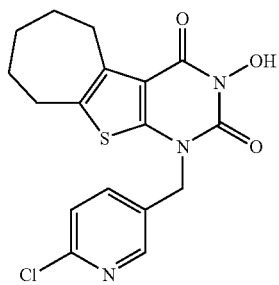

2-Amino-5,6,7,8-tetrahydro-4H-cyclohepta[b]thiophene-3-carboxylic acid ethyl ester was converted to the cyclic intermediate via general procedure A1. The intermediate was alkylated with 2-chloro-5-chloromethyl-pyridine via general procedure B1. Deprotection of this intermediate using general procedure D gave the title compound which was purified by mass triggered preparative HPLC. $^1$H NMR (CDCl$_3$), δ 8.28 (d, J=2.4 Hz, 1H), 7.58 (dd, J=2.4, 8.2 Hz, 1H), 7.11 (d, J=8.2 Hz, 1H), 4.91 (s, 2H), 2.97 (t, J=5.5 Hz, 2H), 2.51 (t, J=5.5 Hz, 2H), 1.68-1.60 (m, 2H), 1.45 (pent., J=5.5 Hz, 4H); Electrospray MS: 378 (M+H); retention time: 2.81 min.

EXAMPLE 40

3-Hydroxy-1-methyl-1,5,6,7,8,9-hexahydro-10-thia-1,3-diaza-benzo[a]azulene-2,4-dione

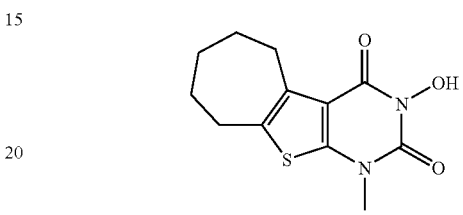

2-Amino-5,6,7,8-tetrahydro-4H-cyclohepta[b]thiophene-3-carboxylic acid ethyl ester was converted to the cyclic intermediate via general procedure A1. The intermediate was alkylated with methyl iodide via general procedure B1. Deprotection of this intermediate using general procedure D gave the title compound which was purified by mass triggered preparative HPLC. $^1$H NMR (DMSO-d6), δ 7.03 (bs, 1H), 3.41 (s, 3H), 3.17 (t, J=5.4 Hz, 2H), 2.77 (t, J=5.4 Hz, 2H), 1.85-1.81 (m, 2H), 1.65-1.57 (m, 4H); Electrospray MS: 267 (M+H); retention time: 2.36 min.

EXAMPLE 41

6-tert-Butyl-3-hydroxy-1-(3-methoxy-benzyl)-1H-thieno[3,2-d]pyrimidine-2,4-dione

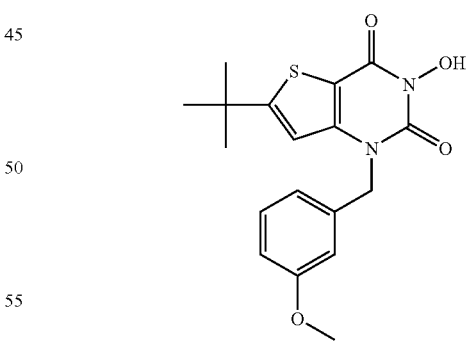

3-Amino-5-tert-butyl-thiophene-2-carboxylic acid ethyl ester was converted to the cyclic intermediate via general procedure A1. The intermediate was alkylated with 1-chloromethyl-3-methoxy-benzene via general procedure B1. Deprotection of this intermediate using general procedure D gave the title compound which was purified by mass triggered preparative HPLC. $^1$H NMR (DMSO-d6), δ 10.45 (bs, 1H), 7.27 (d, J=8.1 Hz, 1H), 7.23 (s, 1H), 6.94 (s, 1H), 6.87-6.84

(m, 2H), 5.23 (s, 2H), 3.73 (s, 3H), 3.32 (s, 2H), 1.34 (s, 9H); Electrospray MS: 361(M+H); retention time: 2.82 min.

EXAMPLE 42

6-tert-Butyl-3-hydroxy-1-naphthalen-2-ylmethyl-1H-thieno[3,2-d]pyrimidine-2,4-dione

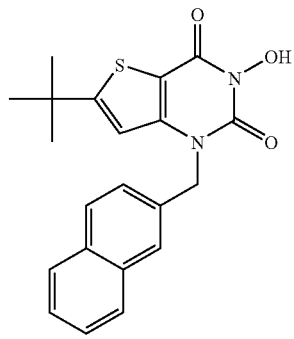

3-Amino-5-tert-butyl-thiophene-2-carboxylic acid ethyl ester was converted to the cyclic intermediate via general procedure A1. The intermediate was alkylated with 2-bromomethyl-naphthalene via general procedure B1. Deprotection of this intermediate using general procedure D gave the title compound which was purified by mass triggered preparative HPLC. ¹H NMR (DMSO-d6), δ 7.05-6.97 (m, 4H), 6.70-6.63 (m, 3H), 6.21 (s, 1H), 4.68 (s, 2H), 0.53 (s, 9H); Electrospray MS: 350 (M+H); retention time: 3.23 min.

EXAMPLE 43

6-tert-Butyl-3-hydroxy-1-thiophen-3-ylmethyl-1H-thieno[3,2-d]pyrimidine-2,4-dione

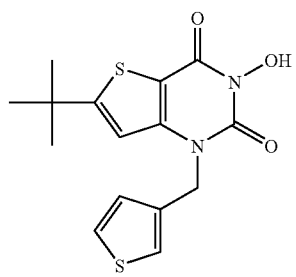

3-Amino-5-tert-butyl-thiophene-2-carboxylic acid ethyl ester was converted to the cyclic intermediate via general procedure A1. The intermediate was alkylated with 3-chloromethyl-thiophene via general procedure B1. Deprotection of this intermediate using general procedure D gave the title compound which was purified by mass triggered preparative HPLC. ¹H NMR (DMSO-d6), δ 7.54-7.50 (m, 2H), 7.31 (s, 1H), 7.09 (d, J=4.8 Hz, 1H), 5.22 (s, 2H), 1.39 (s, 9H); Electrospray MS: 337(+H); retention time: 2.76 min.

EXAMPLE 44

6-tert-Butyl-3-hydroxy-1H-thieno[3,2-d]pyrimidine-2,4-dione

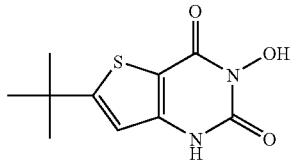

3-Amino-5-tert-butyl-thiophene-2-carboxylic acid ethyl ester was converted to the cyclic intermediate via general procedure A1. Deprotection of this intermediate using general procedure D gave the title compound which was purified by mass triggered preparative HPLC. ¹H NMR (DMSO-d6), δ 6.67 (s, 1H), 1.35 (s, 9H); Electrospray MS: 241(M+H); retention time: 1.94 min.

EXAMPLE 45

5-[6-(4-Chloro-phenyl)-3-hydroxy-2,4-dioxo-3,4-dihydro-2H-thieno[3,2-d]pyrimidin-1-ylmethyl]-furan-2-carboxylic acid methyl ester

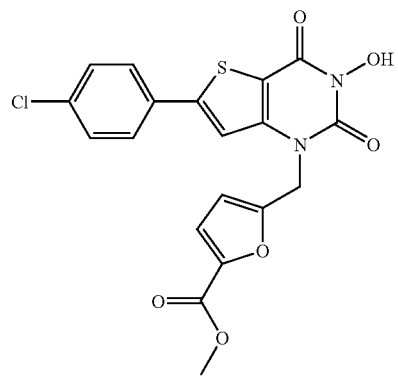

3-Amino-5-(4-chloro-phenyl)-thiophene-2-carboxylic acid ethyl ester was converted to the cyclic intermediate via general procedure A1. The intermediate was alkylated with 5-chloromethyl-furan-2-carboxylic acid methyl ester via general procedure B1. Deprotection of this intermediate using general procedure D gave the title compound which was purified by mass triggered preparative HPLC. ¹H NMR (DMSO-d6), δ 10.90 (bs, 1H), 7.99 (s, 1H), 7.85 (d, J=8.5 Hz, 2H), 7.60 (d, J=8.5 Hz, 2H), 7.25 (d, J=3.6 Hz, 1H), 6.74 (d, J=3.6 Hz, 1H) 5.39 (s, 1H), 3.77 (s, 3H); Electrospray MS: 433(M+H); retention time: 2.94 min.

EXAMPLE 46

3-Hydroxy-1-methyl-1H-benzo[4,5]thieno[3,2-d]pyrimidine-2,4-dione

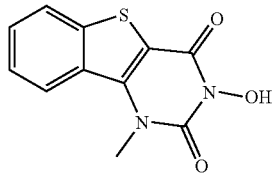

Step a.) 3-Amino-benzo[b]thiophene-2-carboxylic acid methyl ester

2-Fluorobenzonitrile (10 g, 83 mmol) was placed in a round bottom flask equipped with a stir bar followed by anhydrous DMSO (83 ml). Next, Et$_3$N (35 ml, 249 mmol) and methylthioglycolate (83 mmol, 7.42 ml) were added and the reaction mixture was heated to 100° C. After 3 h, the mixture was poured into ice water and the precipitate was filtered and dried providing 12 g (70%) of the title compound as a tan solid: $^1$H NMR (d$_6$-DMSO, 300 MHz) δ 3.81 (s, 3H); 7.18 (br s, 2H); 7.40 (t, J=8 Hz; 1H); 7.51 (dd, J$_1$=8 Hz; J$_2$=1 Hz, 1H); 7.83 (d, J=8 Hz, 1H); 8.14 (d, J=8 Hz, 1H).

Step b.) 3-(2,4-Dimethoxy-benzyloxy)-1H-benzo[4,5]thieno[3,2-d]pyrimidine-2,4-dione 3-Amino-benzo[b]thiophene-2-carboxylic acid methyl ester (1.0 g, 4.8 mmol) was converted to the sub-title compound via general procedure A2. $^1$H NMR (d$_6$-DMSO, 300 MHz) δ3.71 (s, 3H); 3.77 (s, 3H); 5.10 (s, 2H); 6.50-6.57 (m, 2H); 7.43 (d, J=9 Hz, 1H); 7.56 (dd, J=7 Hz, 1H); 7.64 (ddd, J$_1$=8 Hz, J$_2$=1 Hz, 1H); 8.11 (d, J=8 Hz, 1H); 8.36 (d, J=8 Hz, 1H).

Step c.) 3-Hydroxy-1-methyl-1H-benzo[4,5]thieno[3,2-d]pyrimidine-2,4-dione 3-(2,4-Dimethoxy-benzyloxy)-1H-benzo[4,5]thieno[3,2-d]pyrimidine-2,4-dione was alkylated with methyl iodide according to procedure B2. The crude intermediate was deprotected via general procedure D1 to give the title compound which was purified by mass-triggered preparative HPLC. $^1$H NMR (d$_6$-DMSO, 300 MHz) δ 3.76 (s, 3H); 7.33 (dd, J=7 Hz, 1H); 7.42 (dd, J=7 Hz, 1H); 7.93 (d, J=8 Hz, 1H); 8.27 (d, J=8 Hz, 1H); Retention time=1.81 min., m/z=249.0.

EXAMPLE 47

1-Benzyl-3-hydroxy-1H-benzo[4,5]thieno[3,2-d]pyrimidine-2,4-dione

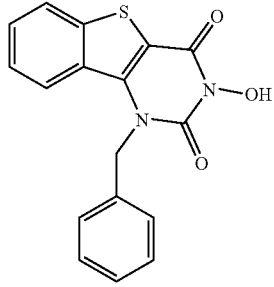

Following general procedure B2 and D1, 3-(2,4-Dimethoxy-benzyloxy)-1H-benzo[4,5]thieno[3,2-d]pyrimidine-2,4-dione was alkylated with benzyl bromide and subsequently deprotected to provide the title compound as a white solid. $^1$H NMR (d$_6$-DMSO, 300 MHz) δ 5.75 (s, 2H); 7.20-7.45 (m, 6H); 7.56 (ddd, J$_1$=8 Hz, J$_2$=1 Hz, 1H); 7.93 (d, J=9 Hz, 1H); 8.15 (d, J=8 Hz, 1H); 11.06 (br s, 1H); retention time=2.57 min., m/z=325.0.

EXAMPLE 48

3-Hydroxy-1-(1-phenyl-ethyl)-1H-benzo[4,5]thieno[3,2-d]pyrimidine-2,4-dione

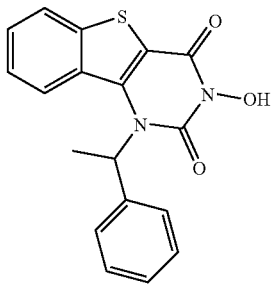

Following general procedure B2 and D1, 3-(2,4-Dimethoxy-benzyloxy)-1H-benzo[4,5]thieno[3,2-d]pyrimidine-2,4-dione was alkylated with (1-Bromoethyl)-benzene and subsequently deprotected to provide the title compound as a white solid. $^1$H NMR (d$_6$-DMSO, 300 MHz) δ 2.16 (d, J=7 Hz, 3H); 6.49 (q, J=7 Hz, 1H); 7.30-7.65 (m, 6H); 7.73 (dd, J=8 Hz, 1H); 8.10 (d, J=8 Hz, 1H); 8.31 (d, J=8 Hz, 1H); 10.80 (br s, 1H); Retention time=2.70 min., m/z=339.0.

EXAMPLE 49

1-(4-tert-Butyl-benzyl)-3-hydroxy-1H-benzo[4,5]thieno[3,2-d]pyrimidine-2,4-dione

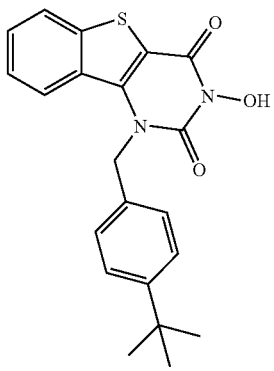

Following general procedure B2 and D1, 3-(2,4-Dimethoxy-benzyloxy)-1H-benzo[4,5]thieno[3,2-d]pyrimidine-2,4-dione (50 mg, 0.13 mmol) was alkylated with 4-tert-butyl benzyl bromide and subsequently deprotected to provide the title compound as a white solid (ret.=3.32 min., m/z=381.0): $^1$H NMR (d$_6$-DMSO, 300 MHz) δ 1.20 (s, 9H);

5.64 (s, 2H); 7.17 (d, J=8 Hz, 1H); 7.25-7.60 (m, 5H); 7.95 (d, J=8 Hz, 1H); 8.08 (d, J=8 Hz, 1H).

EXAMPLE 50

3-Hydroxy-1-propyl-1H-benzo[4,5]thieno[3,2-d]pyrimidine-2,4-dione and 3-Hydroxy-2-propoxy-3H-benzo[4,5]thieno[3,2-d]pyrimidin-4-one

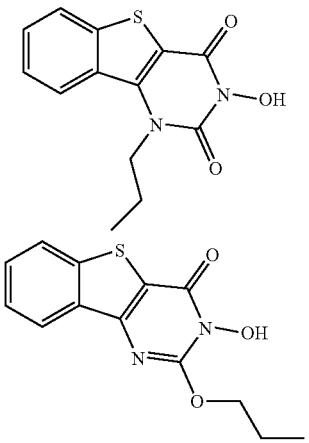

Following general procedure B2,3-(2,4-Dimethoxy-benzyloxy)-1H-benzo[4,5]thieno[3,2-d]pyrimidine-2,4-dione was alkylated with n-iodopropane providing N-alkylated analog and the O-alkylated analog in a 1.6:1 ratio. The mixture was deprotected via general procedure D1 providing the title compounds which could be easily separated by preparative HPLC. N-alkyl product: $^1$H NMR (d$_6$-DMSO, 300 MHz) δ 1.03 (t, J=7 Hz, 3H); 1.81 (sextet, J=7 Hz, 2H); 4.41 (t, J=7 Hz, 2H); 7.58-7.68 (m, 2H); 8.16-8.21 (m, 2H); Retention time=2.26 min., m/z=277.0. O-alkyl product: $^1$H NMR (d$_6$-DMSO, 300 MHz) δ 0.98 (t, J=7 Hz, 3H); 1.79 (sextet, J=7 Hz, 2H); 4.48 (t, J=7 Hz, 2H); 7.56 (dd, J=8 Hz, 1H); 7.64 (dd, J=7 Hz, 1H); 8.10 (d, J=7 Hz, 1H); 8.16 (d, J=8 Hz, 1H); Retention time=2.70 min., m/z=277.0.

EXAMPLE 51

1-Butyl-3-hydroxy-1H-benzo[4,5]thieno[3,2-d]pyrimidine-2,4-dione and 2-Butoxy-3-hydroxy-3H-benzo[4,5]thieno[3,2-d]pyrimidin-4-one

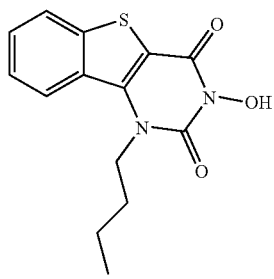

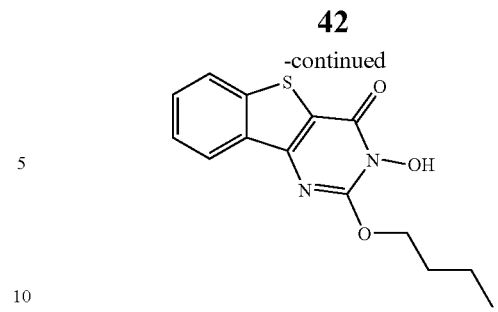

Following general procedure B2,3-(2,4-Dimethoxy-benzyloxy)-1H-benzo[4,5]thieno[3,2-d]pyrimidine-2,4-dione was alkylated with n-iodobutane providing N-alkylated analog and the O-alkylated analog in a 1.6:1 ratio. The mixture was deprotected via general procedure D1 providing the title compounds which could be easily separated by preparative HPLC. N-alkyl product: $^1$H NMR (d$_6$-DMSO, 300 MHz) δ 0.95 (t, J=7 Hz, 3H); 1.47 (sextet, J=7 Hz, 2H); 1.77 (quintet, J=7 Hz, 2H); 4.46 (t, J=7 Hz, 2H); 7.59-7.68 (m, 2H); 8.16-8.23 (m, 2H); $^{13}$C NMR (d$_6$-DMSO, 75 MHz) δ 13.6, 19.1, 30.5, 44.9, 111.8, 124.5, 125.0, 125.8, 128.1, 128.4, 138.2, 140.6, 150.3, 155.5; Retention time=2.54 min., m/z=291.0. O-alkyl product: $^1$H NMR (d$_6$-DMSO, 300 MHz) δ 0.97 (t, J=7 Hz, 3H); 1.48 (sextet, J=7 Hz, 2H); 1.81 (quintet, J=7 Hz, 2H); 4.58 (t, J=7 Hz, 2H); 7.57 (dd, J=8 Hz, 1H); 7.65 (dd, J=8 Hz, 1H); 8.11 (d, J=8 Hz, 1H); 8.17 (d, J=8 Hz, 1H); $^{13}$C NMR (d$_6$-DMSO, 75 MHz) δ 13.5, 18.4, 30.0, 68.7, 115.7, 123.0, 123.8, 125.2, 128.8, 133.4, 140.3, 148.3, 154.4, 155.5; Retention time=3.04 min., m/z=291.0.

EXAMPLE 52

1-(3-Bromo-benzyl)-3-hydroxy-1H-benzo[4,5]thieno[3,2-d]pyrimidine-2,4-dione

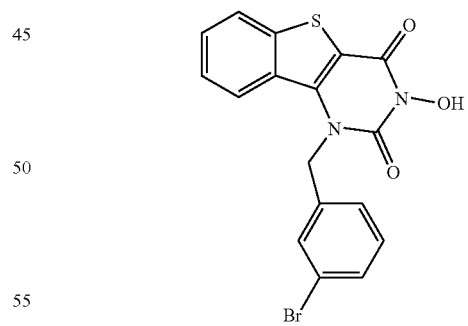

Following general procedure B2 and D1, 3-(2,4-Dimethoxy-benzyloxy)-1H-benzo[4,5]thieno[3,2-d]pyrimidine-2,4-dione was alkylated with 3-bromobenzyl bromide and subsequently deprotected to provide the title compound as a white solid. $^1$H NMR (d$_6$-DMSO, 300 MHz) δ 7.10-7.18 (m, 2H); 7.22 (ddd, J$_1$=8 Hz, J$_2$=1 Hz, 1H); 7.31 (ddd, J$_1$=7 Hz, J$_2$=2 Hz, 1H); 7.39 (dd, J=8 Hz, 1H); 7.44 (s, 1H); 7.71 (d, J=8 Hz, 1H); 7.97 (d, J$_1$=8 Hz, 1H); Ret. time=2.82 min., m/z=403.0.

EXAMPLE 53

1-Biphenyl-2-ylmethyl-3-hydroxy-1H-benzo[4,5]thieno[3,2-d]pyrimidine-2,4-dione

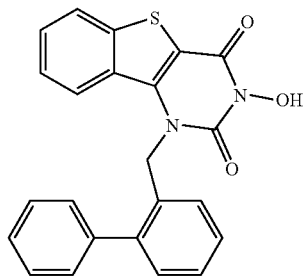

Following general procedure B2 and D1, 3-(2,4-Dimethoxy-benzyloxy)-1H-benzo[4,5]thieno[3,2-d]pyrimidine-2,4-dione was alkylated with 2-phenylbenzyl bromide and subsequently deprotected to provide the title compound as a white solid. $^1$H NMR (d$_6$-DMSO, 300 MHz) δ 5.71 (s, 2H), 7.34 (d, J=8 Hz, 1H), 7.40-7.90 (m, 12H), 8.30 (d, J=8 Hz, 1H); Ret. time=3.22 min., m/z=399.0.

EXAMPLE 54

5-(3-Hydroxy-2,4-dioxo-3,4-dihydro-2H-benzo[4,5]thieno[3,2-d]pyrimidin-1-ylmethyl)-furan-2-carboxylic acid methyl ester

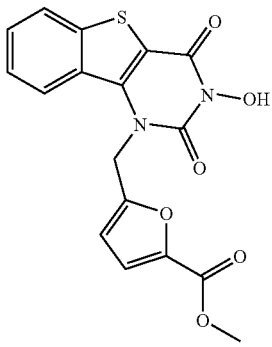

Following general procedure B2 and D1, 3-(2,4-Dimethoxy-benzyloxy)-1H-benzo[4,5]thieno[3,2-d]pyrimidine-2,4-dione was alkylated with methyl 5-chloromethyl-2-furoate and subsequently deprotected to provide the title compound as a white solid. $^1$H NMR (d$_6$-DMSO, 300 MHz) δ 3.64 (s, 3H); 5.60 (s, 2H); 6.48 (d, J=3 Hz, 1H); 7.09 (d, J=3 Hz, 1H); 7.32 (dd, J=8 Hz, 1H); 7.44 (dd, J=8 Hz, 1H); 7.92 (d, J=9 Hz, 1H); 8.00 (d, J=8 Hz, 1H); Ret. time=2.33 min., m/z=373.0.

EXAMPLE 55

3-Hydroxy-1-phenethyl-1H-benzo[4,5]thieno[3,2-d]pyrimidine-2,4-dione

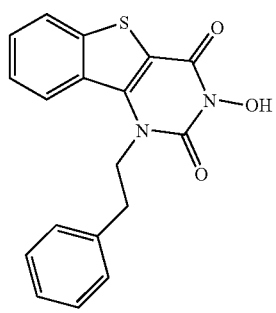

Following general procedure B2 and D1, 3-(2,4-Dimethoxy-benzyloxy)-1H-benzo[4,5]thieno[3,2-d]pyrimidine-2,4-dione was alkylated with 2-Bromoethylbenzene and subsequently deprotected to provide the title compound as a white solid. $^1$H NMR (d$_6$-DMSO, 300 MHz) δ 3.08-3.14 (m, 2H); 4.67-4.73 (m, 2H); 7.24-7.38 (m, 5H); 7.61-7.69 (m, 2H); 8.20 (dd, J$_1$=7 Hz, J$_2$=2 Hz, 1H); 8.30 (dd, J$_1$=7 Hz, J$_2$=2 Hz, 1H); Ret. time=2.77 min., m/z=339.0.

EXAMPLE 56

3-Hydroxy-1-(3-phenyl-allyl)-1H-benzo[4,5]thieno[3,2-d]pyrimidine-2,4-dione

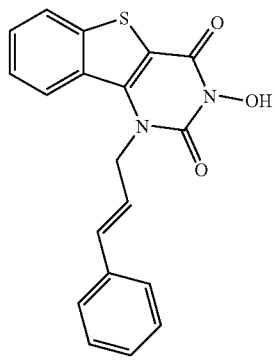

Following general procedure B2 and D1, 3-(2,4-Dimethoxy-benzyloxy)-1H-benzo[4,5]thieno[3,2-d]pyrimidine-2,4-dione was alkylated with trans-cinnamyl chloride and subsequently deprotected to provide the title compound as a white solid. $^1$H NMR (d$_6$-DMSO, 300 MHz) δ 5.24 (s, 1H); 5.25 (s, 1H); 6.51-6.67 (m, 2H); 7.21 (dd, J=7 Hz, 1H); 7.28 (dd, J=8 Hz, 2H); 7.40 (d, J=7 Hz, 2H); 7.53 (dd, J=8 Hz, 1H); 7.61 (dd, J=8 Hz, 1H); 8.16 (d, J=8 Hz, 1H); 8.25 (d, J=8 Hz, 1H), 11.00 (br s, 1H); Ret. time=2.79 min., m/z=350.0.

EXAMPLE 57

3-Hydroxy-1-pyridin-2-ylmethyl-1H-benzo[4,5]thieno[3,2-d]pyrimidine-2,4-dione

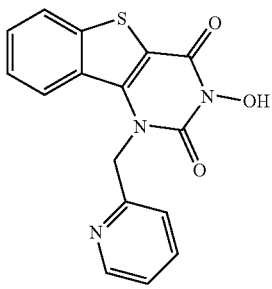

Following general procedure B2 and D1, 3-(2,4-Dimethoxy-benzyloxy)-1H-benzo[4,5]thieno[3,2-d]pyrimidine-2,4-dione was alkylated with 2-chloromethylpyridine hydrochloride and subsequently deprotected to provide the title compound as a white solid.

$^1$H NMR (d$_6$-DMSO, 300 MHz) δ 5.82 (s, 2H); 7.27-7.38 (m, 2H); 7.53 (dd, J=9 Hz, 2H); 7.80 (ddd, J$_1$=8 Hz, J$_2$=2 Hz, 1H); 7.94 (d, J=9 Hz, 1H); 8.13 (d, J=8 Hz, 1H); 8.48 (br d, J=5 Hz, 1H); 11.07 (br s, 1H); Ret. time=2.02 min., m/z=324.0.

EXAMPLE 58

1-(4-Bromo-benzyl)-3-hydroxy-1H-benzo[4,5]thieno[3,2-d]pyrimidine-2,4-dione

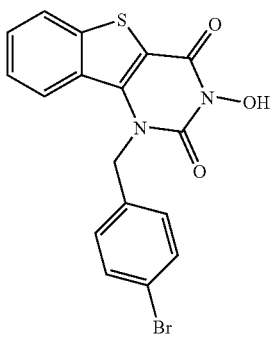

Following general procedure B2 and D1,3-(2,4-Dimethoxy-benzyloxy)-1H-benzo[4,5]thieno[3,2-d]pyrimidine-2,4-dione was alkylated with 4-bromobenzyl bromide and subsequently deprotected to provide the title compound as a white solid. $^1$H NMR (d$_6$-DMSO, 300 MHz) δ 5.77 (s, 2H); 7.39 (d, J=9 Hz, 2H); 7.47 (dd, J=8 Hz, 1H); 7.61-7.66 (m, 3H); 7.96 (d, J=9 Hz, 1H); 8.22 (d, J=8 Hz, 1H); Ret. time=2.89 min., m/z=401.0.

EXAMPLE 59

1-(2-Bromo-benzyl)-3-hydroxy-1H-benzo[4,5]thieno[3,2-d]pyrimidine-2,4-dione

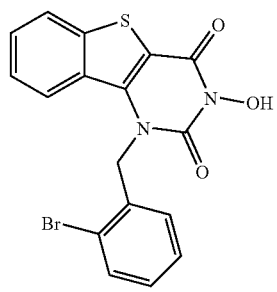

Following general procedure B2 and D1, 3-(2,4-Dimethoxy-benzyloxy)-1H-benzo[4,5]thieno[3,2-d]pyrimidine-2,4-dione was alkylated with 2-bromobenzyl bromide and subsequently deprotected to provide the title compound as a white solid. $^1$H NMR (d$_6$-DMSO, 300 MHz) δ 5.58 (s, 2H); 7.16-7.19 (m, 1H); 7.25-7.31 (m, 2H); 7.34-7.43 (m, 1H); 7.48-7.57 (m, 2H); 7.78-7.81 (m, 1H); 8.43 (d, J=8 Hz, 1H); 11.10 (br s, 1H); Ret. time=2.87 min., m/z=403.0.

EXAMPLE 60

1-Biphenyl-3-ylmethyl-3-hydroxy-1H-benzo[4,5]thieno[3,2-d]pyrimidine-2,4-dione

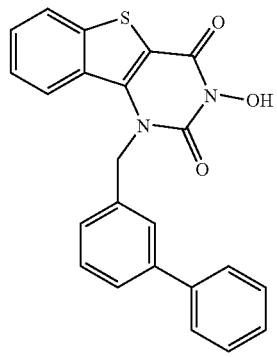

1-(3-Bromo-benzyl)-3-hydroxy-1H-benzo[4,5]thieno[3,2-d]pyrimidine-2,4-dione was treated with phenylboronic acid according to general procedure C. The title compound was obtained as a yellow solid following purification by preparative HPLC. $^1$H NMR (d$_6$-DMSO, 300 MHz) δ 5.79 (s, 2H); 7.26-7.69 (m, 10H); 8.00 (d, J=9 Hz, 1H); 8.13 (d, J=8 Hz, 2H); Ret. time=3.19 min., m/z=399.0.

EXAMPLE 61

1-(4'-Acetyl-biphenyl-4-ylmethyl)-3-hydroxy-1H-benzo[4,5]thieno[3,2-d]pyrimidine-2,4-dione

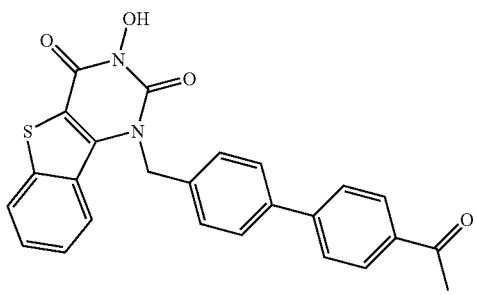

1-(4-Bromo-benzyl)-3-hydroxy-1H-benzo[4,5]thieno[3,2-d]pyrimidine-2,4-dione was treated with 4-acetylphenyl-boronic acid according to general procedure C. The title compound was obtained as a yellow solid following purification by preparative HPLC. $^1$H NMR (d$_6$-DMSO, 300 MHz) δ 2.63 (s, 3H); 5.80 (s, 2H); 7.70-8.20 (m, 12H); Ret. time=2.89, m/z=441.0.

EXAMPLE 62

3-Hydroxy-8-nitro-1H-benzo[4,5]thieno[3,2-d]pyrimidine-2,4-dione

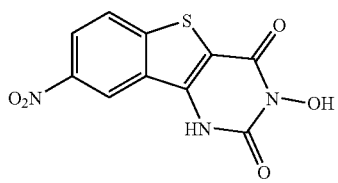

Step a.) 3-(2,4-Dimethoxy-benzyloxy)-8-nitro-1H-benzo[4,5]thieno[3,2-d]pyrimidine-2,4-dione Following general procedure B2,3-amino-5-nitro-benzo[b]thiophene-2-carboxylic acid methyl ester (2.0 g, 7.9 mmol) was combined with toluene (150 ml) and carbonyl diimidazole (1.54 g, 9.5 mmol) and the contents were heated to reflux. Over a 3 hour time period, O-(2,4-Dimethoxy-benzyl)-hydroxylamine (1.87 g, 11.1 mmol) and a 2 M solution of NaOH (24 mmol, 12 ml) were added sequentially. After the usual workup, the precipitate was filtered off, triturated with hot CH$_2$Cl$_2$/MeOH (1:1), filtered, and dried providing 1.56 g (46%) of the sub-title compound. $^1$H NMR (d$_6$-DMSO, 300 MHz) δ3.72 (s, 3H); 3.77 (s, 3H); 5.11 (s, 2H); 6.55-6.58 (m, 2H); 7.43 (d, J=9 Hz, 1H); 8.40 (s, 1H); 8.41 (s, 1H); 9.41 (s, 1H); Ret. time=2.87 min., m/z=428.

Step b.) 3-Hydroxy-8-nitro-1H-benzo[4,5]thieno[3,2-d]pyrimidine-2,4-dione

Following general procedure D1, 3-(2,4-Dimethoxy-benzyloxy)-8-nitro-1H-benzo[4,5]thieno[3,2-d]pyrimidine-2,4-dione was deprotected to provide the title compound as a yellow solid after purification by HPLC. $^1$H NMR (d$_6$-DMSO, 300 MHz) δ8.17-8.25 (m, 2H); 8.98 (d, J=2 Hz, 1H); Ret. time=1.74, m/z=278.

EXAMPLE 63

1-Benzyl-3-hydroxy-8-nitro-1H-benzo[4,5]thieno[3,2-d]pyrimidine-2,4-dione

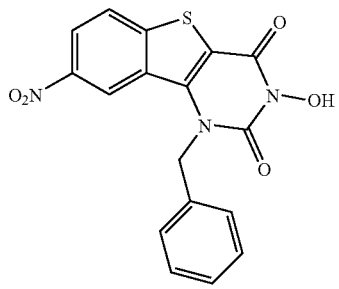

Following general procedure B2 and D1, 3-(2,4-Dimethoxy-benzyloxy)-8-nitro-1H-benzo[4,5]thieno[3,2-d]pyrimidine-2,4-dione was alkylated with benzyl bromide and subsequently deprotected to provide the title compound as a light yellow solid. $^1$H NMR (d$_6$-DMSO, 300 MHz) δ 5.77 (s, 2H); 7.24-7.40 (m, 5H), 8.29 (dd, J$_1$=9 Hz, J$_2$=2 Hz, 1H); 8.40 (d, J=9 Hz, 1H); 8.71 (d, J=2 Hz, 1H); Ret. time=2.56 min., m/z=368.0.

EXAMPLE 64

1-Biphenyl-2-ylmethyl-3-hydroxy-8-nitro-1H-benzo[4,5]thieno[3,2-d]pyrimidine-2,4-dione

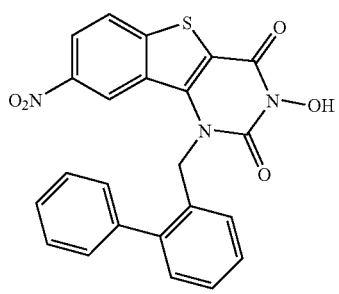

Following general procedure B2 and D1, 3-(2,4-Dimethoxy-benzyloxy)-8-nitro-1H-benzo[4,5]thieno[3,2-d]pyrimidine-2,4-dione was alkylated with 2-phenylbenzyl bromide and subsequently deprotected to provide the title compound as a light yellow solid. $^1$H NMR (d$_6$-DMSO, 300

MHz) δ 5.53 (s, 2H); 7.20-7.57 (m, 9H); 8.29 (dd, $J_1$=9 Hz, $J_2$=2 Hz, 1H); 8.36 (d, J=2 Hz, 1H); 8.40 (d, J=9 Hz, 1H); Ret. time=3.14 min., m/z=444.0.

EXAMPLE 65

3-Hydroxy-7-(3-methoxy-phenyl)-1H-furo[3,2-d]pyrimidine-2,4-dione

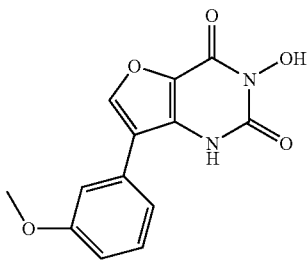

3-methoxy benzyl nitrile was converted to the title compound following general procedure E1, general procedure F, general procedure A2, and general procedure D2. $^1$H NMR (DMSO-$d_6$) δ 10.22 (bs, 1H), 8.32 (s, 1H), 6.88-7.78 (m, 4H), 3.87 (s, 3H); Electrospray MS: 274, obsd. 273 (M–H); retention time: 1.81 min.

EXAMPLE 66

7-Biphenyl-4-yl-3-hydroxy-1H-furo[3,2-d]pyrimidine-2,4-dione

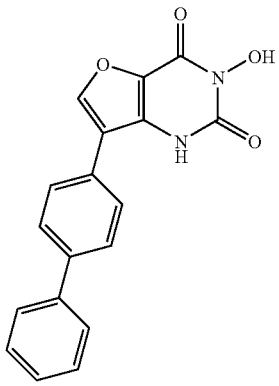

4-bromo benzyl nitrile was converted to the title compound following general procedure E1, general procedure F, general procedure A2, general procedure D2, and general procedure C.

$^1$H NMR (DMSO-$d_6$) δ 10.22 (bs, 1H), 8.40 (s, 1H), 7.35-7.80 (m, 9H); Electrospray MS: 320, obsd. 321 (M+H); retention time: 2.51 min.

EXAMPLE 67

3-Hydroxy-7-(2',5'-dimethoxy-biphenyl-4-yl)-1H-furo[3,2-d]pyrimidine-2,4-dione

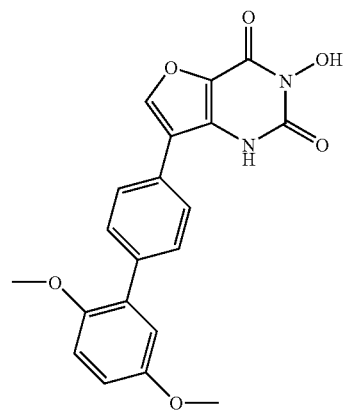

4-bromo benzyl nitrile was converted to the title compound following general procedure E1, general procedure F, general procedure A2, general procedure D2, and general procedure C. $^1$H NMR (DMSO-$d_6$) δ 10.22 (bs, 1H), 8.40 (s, 1H), 7.35-7.80 (m, 9H); Electrospray MS: 380, obsd. 381 (M+H); retention time: 2.47 min.

EXAMPLE 68

1-Benzyl-7-(3-bromo-phenyl)-3-hydroxy-1H-furo[3,2-d]pyrimidine-2,4-dione

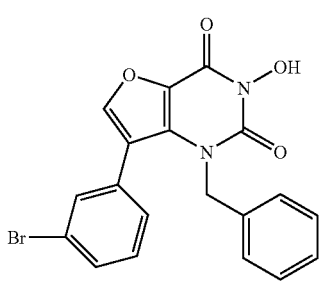

3-Bromo benzyl nitrile was converted to the title compound following general procedure E1, general procedure F, general procedure A2, general procedure D2, and general procedure C.

$^1$H NMR (DMSO-d$_6$) δ 10.22 (bs, 1H), 8.18 (s, 1H), 6.71-7.60 (m, 9H), 4.88 (s, 2H); Electrospray MS: 412, obsd. 413 (M+H); retention time: 2.91 min.

EXAMPLE 69

1-Benzyl-3-hydroxy-7-(3-methoxy-phenyl)-1H-furo[3,2-d]Pyrimidine-2,4-dione

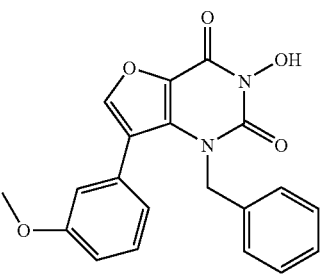

3-Bromo benzyl nitrile was converted to the title compound following general procedure E1, general procedure F, general procedure A2, general procedure D2, and general procedure C.

$^1$HNMR (DMSO-d$_6$) δ 10.22 (bs, 1H), 8.14 (s, 1H), 6.67-7.18 (m, 9H), 4.95 (s, 2H), 3.55 (s, 3H); Electrospray MS: 364, obsd. 365 (M+H); retention time: 2.64 min.

EXAMPLE 70

3-Hydroxy-1-(4-methoxy-benzyl)-7-(3-methoxy-phenyl)-1H-furo[3,2-d]pyrimidine-2,4-dione

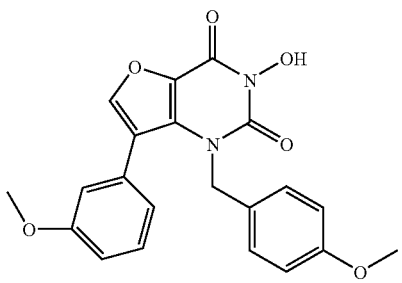

3-Bromo benzyl nitrile was converted to the title compound following general procedure E1, general procedure F, general procedure A2, general procedure D2, and general procedure C.

$^1$HNMR (DMSO-d$_6$) δ 10.22 (bs, 1H), 8.13 (s, 1H), 6.62-7.30 (m, 8H), 4.85 (s, 2H), 3.7 (s, 3H), 3.62 (s, 3H); Electrospray MS: 394, obsd. 395 (M+H); retention time: 2.61 min.

EXAMPLE 71

7-Benzyl-3-hydroxy-1H-furo[3,2-d]pyrimidine-2,4-dione

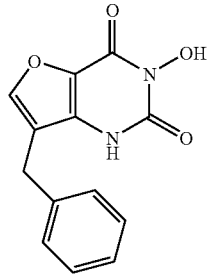

Hydrocinnamonitrile was converted to the title compound following general procedure E2, general procedure F, general procedure A2, and general procedure D2. $^1$H NMR (DMSO-d$_6$) δ 10.22 (bs, 1H), 7.68 (s, 1H), 7.29 (m, 5H), 3.32 (br s, 2H); Electrospray MS: 258, obsd. 259 (M+H); retention time: 1.89 min.

EXAMPLE 72

3-Hydroxy-1H-benzo[4,5]furo[3,2-d]pyrimidine-2,4-dione

Step a.) 3-Amino-benzofuran-2-carboxylic acid methyl ester ortho-Cyanophenol (5.0 g, 41.3 mmol) was placed in a round bottom flask followed by acetone (200 ml) and K$_2$CO$_3$ (6.8 g, 49 mmol). Next, methyl bromoacetate (3.91 ml, 41.3 mmol) was added dropwise at 2° C. and the reaction was heated to reflux. After 4 hours, the reaction was filtered and the acetone was evaporated providing the title compound (7.32 g, 93%) as a white solid. $^1$H NMR (CDCl$_3$, 300 MHz) δ 3.72 (s, 3H); 4.71 (s, 2H); 6.78 (d, J=8 Hz, 1H); 6.99 (t, J=8 Hz, 1H); 7.45 (ddd, J$_1$=8 Hz, J$_2$=1 Hz, 1H); 7.51 (d, J=8 Hz, 1H); Ret. time=2.29 min., ES+m/z=192.

Step a.) 3-(2,4-Dimethoxy-benzyloxy)-1H-benzo[4,5]furo[3,2-d]pyrimidine-2,4-dione Following general procedure B2,3-amino-benzofuran-2-carboxylic acid methyl ester (1.0 g, 5.23 mmol) was combined with toluene (75 ml) and carbonyl diimidazole (1.02 g, 6.3 mmol) and the contents were heated to reflux. Over a 3 hour time period, O-(2,4-Dimethoxy-benzyl)-hydroxylamine (1.24 g, 7.32 mmol) and a 2 M solution of NaOH (10 mmol, 5.0 ml) were added sequentially. After the usual workup, the precipitate was filtered off and dried providing the sub-title compound as a light yellow solid. (1.51 g, 78%) $^{1}$H NMR (d$_{6}$-DMSO, 300 MHz) δ3.74 (s, 3H); 3.77 (s, 3H); 5.07 (s, 2H); 6.54-6.58 (m, 2H); 7.43-7.48 (m, 2H); 7.64 (dd, J=7 Hz, 1H); 7.76 (d, J=8 Hz, 1H); 7.98 (d, J=7 Hz, 1H); Ret. time 2.61 min., m/z=367.

Step b.) 3-Hydroxy-1H-benzo[4,5]furo[3,2-d]pyrimidine-2,4-dione 3-(2,4-Dimethoxy-benzyloxy)-1H-benzo[4,5]furo[3,2-d]pyrimidine-2,4-dione was deprotected according to general procedure D1 to provide the title compound as a white solid.
$^{1}$H NMR (d$_{6}$-DMSO, 300 MHz) δ7.24 (dd, J=7 Hz, 1H); 7.42 (ddd, J$_{1}$=8 Hz, J$_{2}$=7 Hz, J$_{3}$=1 Hz, 1H); 7.53 (d, J=8 Hz, 1H); 7.76 (d, J=8 Hz, 1H); Ret. time=1.41, m/z=218.

EXAMPLE 73

3-Hydroxy-1-(4-methoxy-benzyl)-1H-benzo[4,5]furo[3,2-d]pyrimidine-2,4-dione

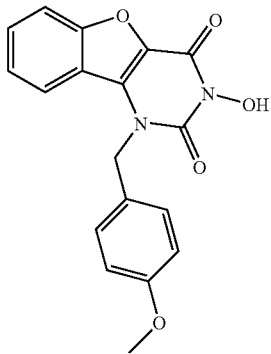

Following general procedure B2 and D1,3-(2,4-Dimethoxy-benzyloxy)-1H-benzo[4,5]furo[3,2-d]pyrimidine-2,4-dione was alkylated with 4-methoxybenzyl chloride and subsequently deprotected to provide the title compound as a white solid. $^{1}$H NMR (d$_{6}$-DMSO, 300 MHz) δ 3.69 (s, 3H); 5.49 (s, 2H); 6.88 (d, J=9 Hz, 2H); 7.25 (d, J=8 Hz, 2H); 7.37 (dd, J=8 Hz, 1H); 7.61 (dd, J=8 Hz, 1H); 7.80 (d, J=8 Hz, 1H); 7.86 (d, J=8 Hz, 1H); Ret. time=2.39 min., m/z=339.0.

EXAMPLE 74

3-Hydroxy-1-(2-methyl-thiazol-4-ylmethyl)-1H-benzo[4,5]furo[3,2-d]pyrimidine-2,4-dione

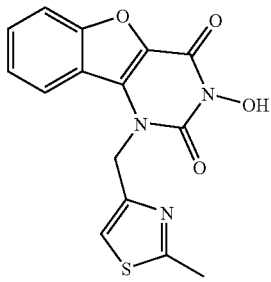

Following general procedure B2 and D1, 3-(2,4-Dimethoxy-benzyloxy)-1H-benzo[4,5]furo[3,2-d]pyrimidine-2,4-dione was alkylated with 4-(chloromethyl)-2-methyl-1,3-thiazole and subsequently deprotected to provide the title compound as a white solid. $^{1}$H NMR (d$_{6}$-DMSO, 300 MHz) δ 2.59 (s, 3H); 5.54 (s, 2H); 7.38 (dd, J=8 Hz, 1H); 7.44 (s, 1H); 7.62 (dd, J=8 Hz, 1H); 7.81 (d, J=8 Hz, 1H); 7.87 (d, J=8 Hz, 1H); Ret. time=2.01 min., m/z=330.0.

EXAMPLE 75

1-Benzyl-3-hydroxy-1H-benzo[4,5]furo[3,2-d]pyrimidine-2,4-dione

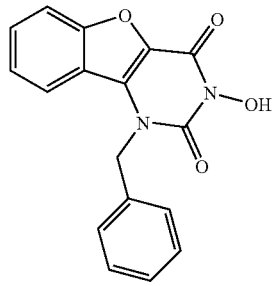

Following general procedure B2 and D1, 3-(2,4-Dimethoxy-benzyloxy)-1H-benzo[4,5]furo[3,2-d]pyrimidine-2,4-dione was alkylated with benzyl bromide and subsequently deprotected to provide the title compound as a white solid. $^{1}$H NMR (d$_{6}$-DMSO, 300 MHz) δ 5.57 (s, 2H); 7.22-7.39 (m, 6H); 7.61 (dd, J=8 Hz, 1H); 7.78-7.82 (m, 2H); Ret. time=2.36 min., m/z=309.0.

EXAMPLE 76

1-Biphenyl-2-ylmethyl-3-hydroxy-1H-benzo[4,5]furo[3,2-d]pyrimidine-2,4-dione

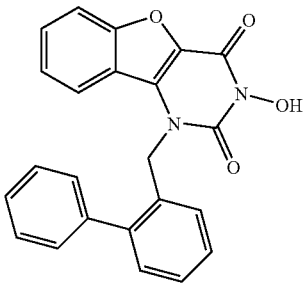

Following general procedure B2 and D1, 3-(2,4-Dimethoxy-benzyloxy)-1H-benzo[4,5]furo[3,2-d]pyrimidine-2,4-dione was alkylated with 2-phenylbenzyl bromide and subsequently deprotected to provide the title compound as a white solid. $^{1}$H NMR (d$_{6}$-DMSO, 300 MHz) δ 5.39 (s, 2H); 7.11 (d, J=7 Hz, 1H); 7.22-7.63 (m, 11H); 7.76 (d, J=8 Hz, 1H); Ret. time=3.01 min., m/z=383.0.

EXAMPLE 77

3-Hydroxy-1-prop-2-ynyl-1H-benzo[4,5]furo[3,2-d]pyrimidine-2,4-dione

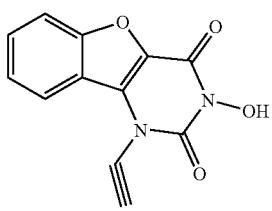

Following general procedure B2 and D1, 3-(2,4-dimethoxy-benzyloxy)-1H-benzo[4,5]furo[3,2-d]pyrimidine-2,4-dione was alkylated with an 80% solution of propargyl bromide in toluene and subsequently deprotected to provide the title compound as a white solid. $^1$H NMR (d$_6$-DMSO, 300 MHz) δ 3.49 (t, J=2 Hz, 1H); 5.15 (d, J=2 Hz, 2H); 7.53 (dd, J=8 Hz, 1H); 7.70 (dd, J=8 Hz, 1H); 7.85 (d, J=8 Hz, 1H); 8.19 (d, J=8 Hz, 1H); Ret. time=1.86 min., m/z=257.0.

EXAMPLE 78

1-Allyl-3-hydroxy-1H-benzo[4,5]furo[3,2-d]pyrimidine-2,4-dione

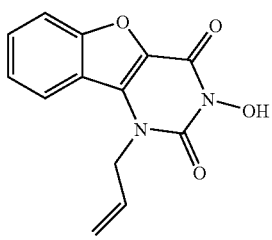

Following general procedure B2 and D1, 3-(2,4-Dimethoxy-benzyloxy)-1H-benzo[4,5]furo[3,2-d]pyrimidine-2,4-dione was alkylated with allyl bromide and subsequently deprotected to provide the title compound as a white solid. $^1$H NMR (d$_6$-DMSO, 300 MHz) δ 4.92-4.94 (m, 2H); 5.09-5.18 (m, 2H); 6.03-6.16 (m, 1H); 7.45 (dd, J=8 Hz, 1H); 7.65 (dd, J=8 Hz, 1H); 7.81 (d, J=8 Hz, 1H); 7.98 (d, J=8 Hz, 1H); Ret. time=1.94 min., m/z=259.0.

EXAMPLE 79

3-Hydroxy-1-(1-phenyl-ethyl)-1H-benzo[4,5]furo[3,2-d]pyrimidine-2,4-dione

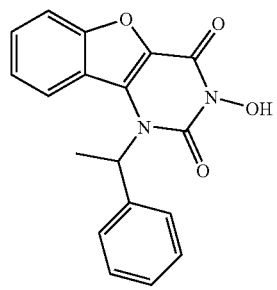

Following general procedure B2 and D1, 3-(2,4-Dimethoxy-benzyloxy)-1H-benzo[4,5]furo[3,2-d]pyrimidine-2,4-dione was alkylated with 1-bromoethyl)benzene and subsequently deprotected to provide the title compound as a white solid. $^1$H NMR (d$_6$-DMSO, 300 MHz) δ 1.98 (d, J=7 Hz, 3H); 6.32 (br s, 1H); 7.25-7.43 (m, 7H); 7.59 (dd, J=8 Hz, 1H); 7.81 (d, J=8 Hz, 1H); Ret. time=2.54 min., m/z=323.0.

EXAMPLE 80

3-Hydroxy-1-(3-phenyl-allyl)-1H-benzo[4,5]furo[3,2-d]pyrimidine-2,4-dione

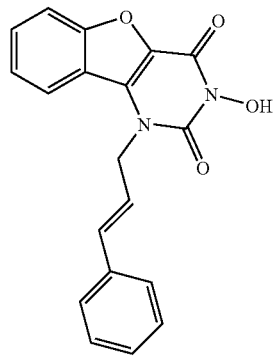

Following general procedure B2 and D1, 3-(2,4-Dimethoxy-benzyloxy)-1H-benzo[4,5]furo[3,2-d]pyrimidine-2,4-dione was alkylated with trans-cinnamyl chloride and subsequently deprotected to provide the title compound as a white solid. $^1$H NMR (d$_6$-DMSO, 300 MHz) δ 5.09 (s, 1H); 5.11 (s, 1H); 6.49-6.58 (m, 2H); 7.18-7.30 (m, 3H);

7.37-7.47 (m, 3H); 7.64 (dd, J=8 Hz, 1H); 7.82 (d, J=8 Hz, 1H); 8.07 (d, J=8 Hz, 1H), 10.73 (br s, 1H); Ret. time=2.66 min, m/z=333.0.

EXAMPLE 81

1-(2-Bromo-benzyl)-3-hydroxy-1H-benzo[4,5]furo[3,2-d]pyrimidine-2,4-dione

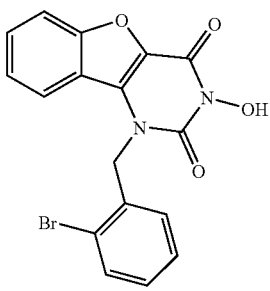

Following general procedure B2 and D1,3-(2,4-dimethoxy-benzyloxy)-1H-benzo[4,5]furo[3,2-d]pyrimidine-2,4-dione was alkylated with 2-bromobenzyl bromide and subsequently deprotected to provide the title compound as a white solid. $^1$H NMR (d$_6$-DMSO, 300 MHz) δ 5.46 (s, 2H); 7.09-7.13 (m, 1H); 7.23-7.27 (m, 2H); 7.32-7.37 (m, 2H); 7.56-7.62 (m, 1H); 7.74-7.78 (m, 1H); 7.82 (d, J=8 Hz, 1H); Ret. time=2.72 min., m/z=387.0.

EXAMPLE 82

1-(3-Bromo-benzyl)-3-hydroxy-1H-benzo[4,5]furo[3,2-d]pyrimidine-2,4-dione

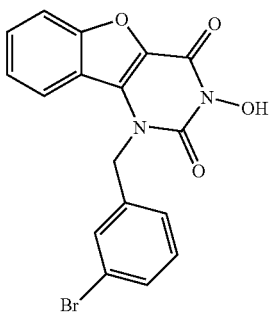

Following general procedure B2 and D1, 3-(2,4-dimethoxy-benzyloxy)-1H-benzo[4,5]furo[3,2-d]pyrimidine-2,4-dione was alkylated with 3-bromobenzyl bromide and subsequently deprotected to provide the title compound as a white solid. $^1$H NMR (d$_6$-DMSO, 300 MHz) δ 5.55 (s, 2H); 7.25-7.40 (m, 3H); 7.42-7.52 (m, 1H); 7.57-7.63 (m, 2H); 7.76-7.85 (m, 2H); Ret. time=2.64 min., m/z=386.0.

EXAMPLE 83

1-(4-Bromo-benzyl)-3-hydroxy-1H-benzo[4,5]furo[3,2-d]pyrimidine-2,4-dione

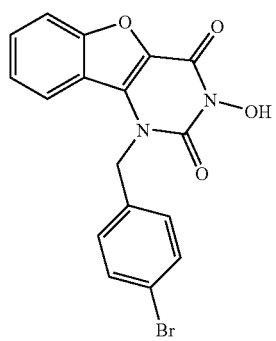

Following general procedure B2 and D1, 3-(2,4-dimethoxy-benzyloxy)-1H-benzo[4,5]furo[3,2-d]pyrimidine-2,4-dione was alkylated with 4-bromobenzyl bromide and subsequently deprotected to provide the title compound as a white solid. $^1$H NMR (d$_6$-DMSO, 300 MHz) δ 5.52 (s, 2H); 7.29-7.40 (m, 3H); 7.52 (d, J=8 Hz, 2H); 7.60 (dd, J=8 Hz, 1H); 7.75-7.81 (m, 2H); Ret. time=2.70 min., m/z=387.0.

EXAMPLE 84

1-(2,5-Difluorobiphenyl)-2-ylmethyl-3-hydroxy-1H-benzo[4,5]furo[3,2-d]pyrimidine-2,4-dione

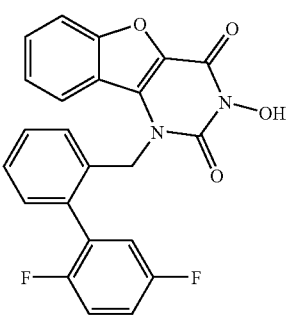

1-(2-Bromo-benzyl)-3-hydroxy-1H-benzo[4,5]furo[3,2-d]pyrimidine-2,4-dione was treated with 2,5-difluorophenylboronic acid according to general procedure C to provide the title compound as a yellow solid. $^1$H NMR (d$_6$-DMSO, 300

MHz) δ5.32 (s, 2H); 7.15-7.19 (m, 1H); 7.23-7.48 (m, 7H); 7.48-7.61 (m, 2H); 7.79 (d, J=8 Hz, 1H); Ret. time=3.06, m/z=421.0.

EXAMPLE 85

1-(3-Benzo[1,3]dioxol-5-yl-benzyl)-3-hydroxy-1H-benzo[4,5]furo[3,2-d]pyrimidine-2,4-dione

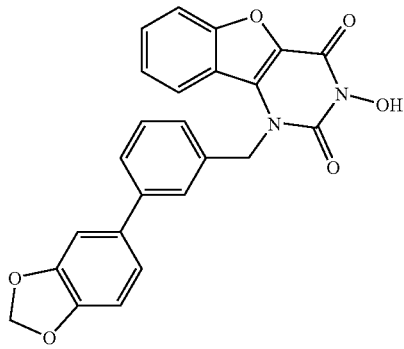

1-(2-Bromo-benzyl)-3-hydroxy-1H-benzo[4,5]furo[3,2-d]pyrimidine-2,4-dione was treated with 3,4-methylenedioxyphenylboronic acid according to general procedure C to provide the title compound as a yellow solid. $^1$H NMR (d$_6$-DMSO, 300 MHz) δ5.61 (s, 2H); 6.05 (s, 2H); 6.98 (d, J=8 Hz, 1H); 7.10 (dd, J$_1$=8 Hz, J$_2$=2 Hz, 1H); 7.18-7.21 (m, 2H); 7.35 (dd, J=8 Hz, 2H); 7.49 (br d, J=8 Hz, 1H); 7.57-7.62 (m, 2H); 7.80 (d, J=8 Hz, 1H); 7.87 (d, J=8 Hz, 1H); Ret. time=2.95 min., m/z=429.0.

EXAMPLE 86

4'-(3-Hydroxy-2,4-dioxo-3,4-dihydro-2H-benzo[4,5]furo[3,2-d]pyrimidin-1-ylmethyl)-biphenyl-3-carboxylic acid amide

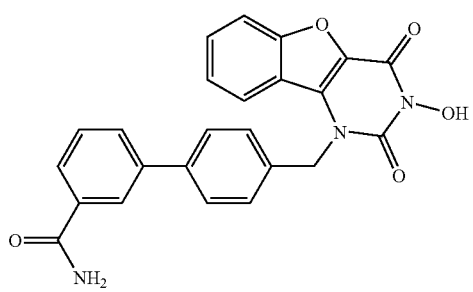

1-(2-Bromo-benzyl)-3-hydroxy-1H-benzo[4,5]furo[3,2-d]pyrimidine-2,4-dione was treated with 3-acetaminophenylboronic acid according to general procedure C to provide the title compound as a yellow solid. $^1$H NMR (d$_6$-DMSO, 300

MHz) δ5.63 (s, 2H); 7.32-7.54 (m, 4H); 7.59-7.71 (m, 3H); 7.76-7.89 (m, 3H); 7.93-8.11 (m, 2H); Ret. time=2.20 min., m/z=427.0.

EXAMPLE 87

7-Diethylamino-3-hydroxy-1H-benzo[4,5]furo[3,2-d]pyrimidine-2,4-dione

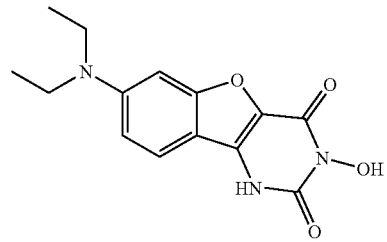

Step a.) 3-Amino-6-diethylamino-benzofuran-2-carboxylic acid methyl ester

4-Diethylamino-2-hydroxy-benzonitrile (350 mg, 2.63 mmol) was placed in a round bottom flask followed by acetone (17 ml) and K$_2$CO$_3$ (490 mg, 3.55 mmol). Next, methyl bromoacetate (320 Ml, 3.38 mmol) was added dropwise at 22° C. and the reaction was stirred at 22° C. After 24 hours, the reaction was filtered and concentrated providing intermediate cyanoester 531 mg (77%). This reaction was carried out twice providing a total 1.23 g of the intermediate cyanoester. Next, the cyanoester (1.23 g, 4.7 mmol) was dissolved in anhydrous DMSO and added dropwise to a suspension of NaH (60% dispersion in oil) (118 mg, 4.93 mmol) in anhydrous DMSO (2.3 ml). After 15 min., the reaction mixture was poured into ice water (100 ml) and extracted with EtOAc (5×75 ml). The organic layer was dried (MgSO$_4$), filtered and concentrated providing a dark green oil. This crude oil was chromatographed on silica gel (hexane/EtOAc 4:1) providing the sub-title compound (415 mg, 34%) as a green solid: $^1$H NMR (CDCl$_3$, 300 MHz) δ 1.11 (t, J=7 Hz, 6H); 3.39 (q, J=7 Hz, 4H); 3.74 (s, 3H); 6.21 (br s, 2H); 6.53 (d, J=2 Hz, 1H); 6.67 (dd, J$_1$=9 Hz, J$_2$=2 Hz, 1H); 7.64 (d, J=9 Hz, 1H).

Step b.) 7-Diethylamino-3-(2,4-dimethoxy-benzyloxy)-1H-benzo[4,5]furo[3,2-d]pyrimidine-2,4-dione Following general procedure B2, 3-amino-6-diethylamino-benzofuran-2-carboxylic acid methyl ester (300 g, 1.14 mmol) was combined with toluene (24 ml) and carbonyl diimidazole (227 mg, 1.4 mmol) and the contents were heated to reflux. Over a 3 h time period, O-(2,4-Dimethoxy-benzyl)-hydroxylamine (270 mg, 1.6 mmol) and a 2 M solution of NaOH (2.4 mmol, 1.2 ml) were added sequentially. After the usual workup, the precipitate was filtered off and dried providing 251 mg (50%) of the sub-title compound as a light brown solid: $^1$HNMR (d$_6$-DMSO, 300 MHz) δ1.13 (t, J=7 Hz, 6H); 3.44 (q, J=7 Hz, 4H); 3.74 (s, 3H); 3.77 (s, 3H); 5.04 (s, 2H); 6.54-6.56 (m, 2H); 6.81 (br s, 1H); 6.84 (dd, J$_1$=9 Hz, J$_2$=2 Hz, 1H); 7.42 (d, J=9 Hz, 1H); 7.69 (d, J=9 Hz, 1H).

Step c.) 7-Diethylamino-3-hydroxy-1H-benzo[4,5]furo[3,2-d]pyrimidine-2,4-dione

7-Diethylamino-3-(2,4-dimethoxy-benzyloxy)-1H-benzo[4,5]furo[3,2-d]pyrimidine-2,4-dione was deprotected according to general procedure D-1 providing the title compound as a white solid. $^1$H NMR (d$_6$-DMSO, 300 MHz) δ1.13 (t, J=7 Hz, 6H); 3.43 (q, J=7 Hz, 4H); 6.79 (d, J=2 Hz, 1H);

6.85 (dd, $J_1$=9 Hz, $J_2$=2 Hz, 1H); 7.68 (d, J=9 Hz, 1H); 10.45 (br s, 1H); Ret. time=2.17 min., m/z=289.0.

EXAMPLE 88

1-Benzyl-7-diethylamino-3-hydroxy-1H-benzo[4,5]furo[3,2-d]pyrimidine-2,4-dione

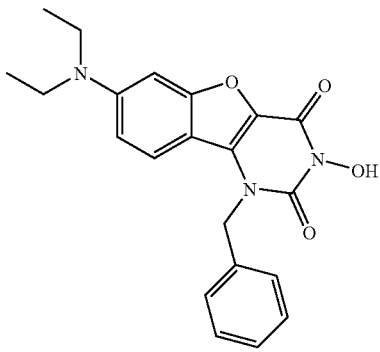

Following general procedure B2 and D1, 7-Diethylamino-3-(2,4-dimethoxy-benzyloxy)-1H-benzo[4,5]furo[3,2-d]pyrimidine-2,4-dione was alkylated with benzyl bromide and subsequently deprotected to provide the title compound as a white solid. $^1$H NMR ($d_6$-DMSO, 300 MHz) δ1.09 (t, J=7 Hz, 6H); 3.34-3.47 (m, 4H); 5.48 (s, 2H); 6.69-6.83 (m, 2H); 7.24-7.37 (m, 5H); 7.48 (d, J=9 Hz, 1H); 10.75 (br s, 1H); Ret. time=2.97 min., m/z=380.0.

EXAMPLE 89

Determination of IC50 of Compounds Against FEN1 and XPG

FEN1 and XPG inhibition assays are performed using a fluorogenic substrate consisting of a triple-labeled double-stranded DNA molecule containing an internal 2-nucleotide gap. This molecule, referred to as BVT substrate, is prepared by annealing oligonucleotide VT (5'-VIC-ccctccgc-cgtcgcgttt-TAMRA; Applied BioSystems) with oligonucleotide B (5'-aaacgcgacggcggagggtcttgctcagtgtc gtctccgacact-gagcaa-Black Hole Quencher; Integrated DNA Technologies). FEN1 will act on the BVT substrate, thereby separating the quenchers from the fluorescent moiety, VIC. This results in increased fluorescent signal. High-throughput enzyme inhibition assays are performed using 60 µl reaction mixes (50 mM Tris-HCl; pH 8.0, 10 mM $MgCl_2$, 0.5 mM 2-ME, 6 µg BSA, 2.5 µg circular plasmid, 180 U FEN1 or 50 ng XPG, 25 µM test compound, and 5 pmol BVT substrate) contained in black 96-well plates. Reactions are incubated at room temperature for 90 minutes, stopped through the addition of 40 µl stop buffer (0.025% SDS, 12.5 mM EDTA) and fluorescence is measured using a Fluoroscan plate-reading fluorometer fitted with 485 nm excitation/538 nm emission filters.

The invention claimed is:

1. A compound of the formula

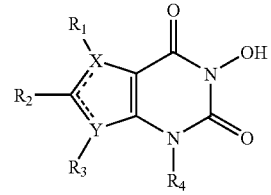

(I)

where X and Y may be C, O or S provided that one of X and Y must be C;

$R_1$ which is present when X is C is selected from the group consisting of H, aryl, heteroaryl, wherein said heteroaryl is selected from the group consisting of furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzothiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl, alkyl, alkylaryl, fused aryl with $R_2$, and fused cycloalkyl with $R_2$;

$R_2$ is selected from the group consisting of H, aryl, heteroaryl, wherein said heteroaryl consists of C, N, O and S atoms, alkyl, alkylaryl, fused aryl with $R_1$ or $R_3$, and fused cycloalkyl with $R_1$ or $R_3$;

$R_3$ which is present when Y is C is selected from the group consisting of H, aryl, heteroaryl, wherein said heteroaryl consists of C, N, O and S atoms, alkyl, alkylaryl, fused aryl with $R_2$, and fused cycloalkyl with $R_2$; and $R_4$ is selected from the group consisting of alkyl, aryl, heteroaryl, wherein said heteroaryl consists of C, N, O and S atoms, and alkylaryl;

or a pharmaceutically acceptable salt or isomer thereof.

2. A compound as in claim 1 of the formula

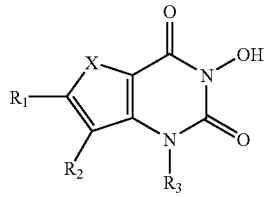

where $R_1$ is H, alkyl, aryl or a fused aryl or alkyl ring with $R_2$;

$R_2$ is H, alkyl, aryl or a fused aryl or cycloalkyl ring with $R_1$;

$R_3$ is alkyl or aryl; and

X is S or O.

3. A compound as in claim 1 of the formula

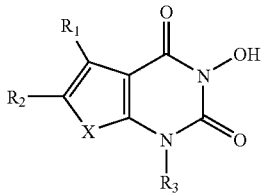

where $R_1$ is H, alkyl, aryl or a fused aryl or alkyl ring with $R_2$; $R_2$ is H, alkyl, aryl or a fused aryl or cycloalkyl ring with $R_1$; $R_3$ is alkyl or aryl; and X is S or O.

4. A compound of the formula

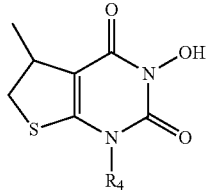

wherein $R_4$ is substituted benzyl; or a pharmaceutically acceptable salt or isomer thereof.

5. A compound selected from the group consisting of 3-Hydroxy-1H-thieno[2,3-d]pyrimidine-2,4-dione;
3-Hydroxy-1,5,6,7,8,9-hexahydro-10-thia-1,3-diaza-benzo[a]azulene-2,4-dione;
1-Benzyl-3-hydroxy-5-methyl-1H-thieno[2,3-d]pyrimidine-2,4-dione ;
3-Hydroxy-1-(7-methoxy-benzo[1,3]dioxol-5-ylmethyl)-5-methyl-1H-thieno[2,3-d ]pyrimidine-2,4-dione;
3-Hydroxy-5-methyl-1-(2,4,5-trimethoxy-benzyl)-1H-thieno[2,3-d]pyrimidine;
1-(6-Chloro-pyridin-3-ylmethyl)-3-hydroxy-5-methyl-1H-thieno[2,3-d]pyrimidine-2,4-dione;
3-Hydroxy-5-methyl-1-quinolin-2-ylmethyl-1H-thieno [2,3-d]pyrimidine-2,4-dione;
3-Hydroxy-5-methyl-1-(2-thiophen-2-yl-thiazol-4-ylmethyl)-1H-thieno[2,3-d]pyrimidine-2,4-dione;
3-Hydroxy-1-naphthalen-2-ylmethyl-1H-thieno[2,3-d] pyrimidine-2,4-dione;
3-Hydroxy-6-phenyl-1H-thieno[3,2-d]pyrimidine-2,4-dione;
3-Hydroxy-6-phenyl-1-(tetrahydro-furan-2-ylmethyl)-1H-thieno[3,2-d]pyrimidine-2,4-dione;
3-Hydroxy-7-phenyl-1H-thieno[3,2-d]pyrimidine-2,4-dione;
1-(3-Bromo-benzyl)-3-hydroxy-1H-thieno[3,2-d]pyrimidine-2,4-dione;
3-Hydroxy-1-naphthalen-2-ylmethyl-1H-thieno[3,2-d] pyrimidine-2,4-dione;
1-(2-Chloro-benzyl)-3-hydroxy-1H-thieno[3,2-d]pyrimidine-2,4-dione;
3'-(3-Hydroxy-2,4-dioxo-3,4-dihydro-2H-thieno[3,2-d] pyrimidin-1-ylmethyl)-biphenyl-4-carboxylic acid amide;
1-(3'-Acetyl-biphenyl-3-ylmethyl)-3-hydroxy-1H-thieno [3,2-d]pyrimidine-2,4-dione;
N-[3'-(3-Hydroxy-2,4-dioxo-3,4-dihydro-2H-thieno[3,2-d]pyrimidin-1-ylmethyl)-biphenyl-3-yl]-acetamide;
1-(6-Chloro-pyridin-3-ylmethyl)-3-hydroxy-1H-thieno[3,2-d]pyrimidine-2,4-dione;
3-Hydroxy-1-[6-(4-trifluoromethoxy-phenyl)-pyridin-3-ylmethyl]-1H-thieno[3,2-d ]pyrimidine-2,4-dione;
3-Hydroxy-1-[6-(2-trifluoromethyl-phenyl)-pyridin-3-ylmethyl]-1H-thieno[3,2-d]pyrimidine-2,4-dione;
1-[6-(3,3-Dimethyl-but-1-enyl)-pyridin-3-ylmethyl]-3-hydroxy-1H-thieno[3,2-d]pyrimidine-2,4-dione;
3-Hydroxy-1H-benzo[4,5]thieno[3,2-d]pyrimidine-2,4-dione;
3-Hydroxy-1-(2-pyrrolidin-1-yl-ethyl)-1H-thieno[3,2-d] pyrimidine-2,4-dione;
3-Hydroxy-7-methyl-1-(4-methyl-benzyl)-1H-thieno[3,2-d]pyrimidine-2,4-dione;
3-Hydroxy-7-methyl-1-(3-methyl-benzyl)-1H-thieno[3,2-d]pyrimidine-2,4-dione;
1-(4-Bromo-benzyl)-3-hydroxy-7-methyl-1H-thieno[3,2-d]pyrimidine-2,4-dione;
1-(2'-Acetyl-biphenyl-4-ylmethyl)-3-hydroxy-7-methyl-1H-thieno[3,2-d]pyrimidine-2,4-dione;
5-(4-Bromo-phenyl)-3-hydroxy-1H-thieno[2,3-d]pyrimidine-2,4-dione;
7-Benzenesulfonyl-3-hydroxy-1H-thieno[3,2-d]pyrimidine-2,4-dione;
3-Hydroxy-7-phenyl-6-trifluoromethyl-1H-thieno[3,2-d] pyrimidine-2,4-dione;
3-Hydroxy-1-(4-methoxy-benzyl)-7-phenyl-1H-thieno[3,2-d]pyrimidine-2,4-dione;
3-Hydroxy-1-(4-methoxy-benzyl)-7-phenyl-1H-thieno[3,2-d]pyrimidine-2,4-dione;
1-(6-Chloro-pyridin-3-ylmethyl)-3-hydroxy-7-phenyl-1H-thieno[3,2-d]pyrimidine-2,4-dione;
-Hydroxy-7-phenyl-1-(3,4,5-trimethoxy-benzyl)-1H-thieno[3,2-d]pyrimidine-2,4-dione' 3-Hydroxy-7-phenyl-1-thiophen-3-ylmethyl-1H-thieno[3,2-d]pyrimidine-2,4-dione;
3-Hydroxy-1-(4-methoxy-benzyl)-1,5,6,7,8,9-hexahydro-10-thia-1,3-diaza-benzo [a]azulene-2,4-dione;
3-Hydroxy-1-thiophen-3-ylmethyl-1,5,6,7,8,9-hexahydro-10-thia-1,3-diaza-benzo [a]azulene-2,4-dione;
1-(6-Chloro-pyridin-3-ylmethyl)-3-hydroxy-1,5,6,7,8,9-hexahydro-10-thia-1,3-diaza-benzo [a]azulene-2,4-dione;
3-Hydroxy-1-methyl-1,5,6,7,8,9-hexahydro-10-thia-1,3-diaza-benzo[a]azulene-2,4-dione;
6-tert-Butyl-3-hydroxy-1-(3-methoxy-benzyl)-1H-thieno [3,2-d]pyrimidine-2,4-dione;
6-tert-Butyl-3-hydroxy-1-naphthalen-2-ylmethyl-1H-thieno[3,2-d]pyrimidine-2,4-dione;
6-tert-Butyl-3-hydroxy-1-thiophen-3-ylmethyl-1H-thieno [3,2-d]pyrimidine-2,4-dione;
6-tert-Butyl-3-hydroxy-1H-thieno[3,2-d]pyrimidine-2,4-dione;
5-[6-(4-Chloro-phenyl)-3-hydroxy-2,4-dioxo-3,4-dihydro-2H-thieno[3,2-d]pyrimidin-1-ylmethyl ]-furan-2-carboxylic acid methyl ester;
3-Hydroxy-1-methyl-1H-benzo[4,5]thieno[3,2-d]pyrimidine-2,4-dione;
1-Benzyl-3-hydroxy-1H-benzo[4,5]thieno[3,2-d]pyrimidine-2,4-dione;
3-Hydroxy-1-(1-phenyl-ethyl)-1H-benzo[4,5]thieno[3,2-d]pyrimidine-2,4-dione;
1-(4-tert-Butyl-benzyl)-3-hydroxy-1H-benzo[4,5]thieno [3,2-d]pyrimidine-2,4-dione;
3-Hydroxy-1-propyl-1H-benzo[4,5]thieno[3,2-d]pyrimidine-2,4-dione and 3-Hydroxy-2-propoxy -3H-benzo[4,5]thieno[3,2-d]pyrimidin-4-one;

1-Butyl-3-hydroxy-1H-benzo[4,5]thieno[3,2-d]pyrimidine-2,4-dione and 2-Butoxy-3-hydroxy-3H-benzo[4,5]thieno[3,2-d]pyrimidin-4-one;
1-(3-Bromo-benzyl)-3-hydroxy-1H-benzo[4,5]thieno[3,2-d]pyrimidine-2,4-dione;
1-Biphenyl-2-ylmethyl-3-hydroxy-1H-benzo[4,5]thieno[3,2-d]pyrimidine-2,4-dione;
5-(3-Hydroxy-2,4-dioxo-3,4-dihydro-2H-benzo[4,5]thieno[3,2-d]pyrimidin-1-ylmethyl)-furan-2-carboxylic acid methyl ester;
3-Hydroxy-1-phenethyl-1H-benzo[4,5]thieno[3,2-d]pyrimidine-2,4-dione;
3-Hydroxy-1-(3-phenyl-allyl)-1H-benzo[4,5]thieno[3,2-d]pyrimidine-2,4-dione;
3-Hydroxy-1-pyridin-2-ylmethyl-1H-benzo[4,5]thieno[3,2-d]pyrimidine-2,4-dione;
1-(4-Bromo-benzyl)-3-hydroxy-1H-benzo[4,5]thieno[3,2-d]pyrimidine-2,4-dione;
1-(2-Bromo-benzyl)-3-hydroxy-1H-benzo[4,5]thieno[3,2-d]pyrimidine-2,4-dione;
1-Biphenyl-3-ylmethyl-3-hydroxy-1H-benzo[4,5]thieno[3,2-d]pyrimidine-2,4-dione;
1-(4'-Acetyl-biphenyl-4-ylmethyl)-3-hydroxy-1H-benzo[4,5]thieno[3,2-d]pyrimidine-2,4-dione;
3-Hydroxy-8-nitro-1H-benzo[4,5]thieno[3,2-d]pyrimidine-2,4-dione;
1-Benzyl-3-hydroxy-8-nitro-1H-benzo[4,5]thieno[3,2-d]pyrimidine-2,4-dione;
1-Biphenyl-2-ylmethyl-3-hydroxy-8-nitro-1H-benzo[4,5]thieno[3,2-d]pyrimidine-2,4-dione;
3-Hydroxy-7-(3-methoxy-phenyl)-1H-furo[3,2-d]pyrimidine-2,4-dione;
7-Biphenyl-4-yl-3-hydroxy-1H-furo[3,2-d]pyrimidine-2,4-dione;
7-Biphenyl-4-yl-3-hydroxy-1H-furo[3,2-d]pyrimidine-2,4-dione;
1-Benzyl-7-(3-bromo-phenyl)-3-hydroxy-1H-furo[3,2-d]pyrimidine-2,4-dione;
1-Benzyl-7-(3-bromo-phenyl)-3-hydroxy-1H-furo[3,2-d]pyrimidine-2,4-dione;
3-Hydroxy-1-(4-methoxy-benzyl)-7-(3-methoxy-phenyl)-1H-furo[3,2-d]pyrimidine-2,4-dione;
7-Benzyl-3-hydroxy-1H-furo[3,2-d]pyrimidine-2,4-dione;
3-Hydroxy-1H-benzo[4,5]furo[3,2-d]pyrimidine-2,4-dione;
3-Hydroxy-1-(4-methoxy-benzyl)-1H-benzo[4,5]furo[3,2-d]pyrimidine-2,4-dione;
3-Hydroxy-1-(2-methyl-thiazol-4-ylmethyl)-1H-benzo[4,5]furo[3,2-d]pyrimidine-2,4-dione;
3-Hydroxy-1-(2-methyl-thiazol-4-ylmethyl)-1H-benzo[4,5]furo[3,2-d]pyrimidine-2,4-dione;
1-Biphenyl-2-ylmethyl-3-hydroxy-1H-benzo[4,5]furo[3,2-d]pyrimidine-2,4-dione;
3-Hydroxy-1-prop-2-ynyl-1H-benzo[4,5]furo[3,2-d]pyrimidine-2,4-dione;
1-Allyl-3-hydroxy-1H-benzo[4,5]furo[3,2-d]pyrimidine-2,4-dione;
3-Hydroxy-1-(1-phenyl-ethyl)-1H-benzo[4,5]furo[3,2-d]pyrimidine-2,4-dione;
3-Hydroxy-1-(3-phenyl-allyl)-1H-benzo[4,5]furo[3,2-d]pyrimidine-2,4-dione;
1-(2-Bromo-benzyl)-3-hydroxy-1H-benzo[4,5]furo[3,2-d]pyrimidine-2,4-dione;
1-(3-Bromo-benzyl)-3-hydroxy-1H-benzo[4,5]furo[3,2-d]pyrimidine-2,4-dione;
1-(4-Bromo-benzyl)-3-hydroxy-1H-benzo[4,5]furo[3,2-d]pyrimidine-2,4-dione;
1-(2,5-Difluorobiphenyl)-2-ylmethyl-3-hydroxy-1H-benzo[4,5]furo[3,2-d]pyrimidine-2,4-dione;
1-(3-Benzo[1,3]dioxol-5-yl-benzyl)-3-hydroxy-1H-benzo[4,5]furo[3,2-d]pyrimidine-2,4-dione;
4'-(3-Hydroxy-2,4-dioxo-3,4-dihydro-2H-benzo[4,5]furo[3,2-d]pyrimidin-1-ylmethyl)-biphenyl-3-carboxylic acid amide;
7-Diethylamino-3-hydroxy-1H-benzo[4,5]furo[3,2-d]pyrimidine-2,4-dione; and
1-Benzyl-7-diethylamino-3-hydroxy-1H-benzo[4,5]furo[3,2-d]pyrimidine-2,4-dione.

6. A pharmaceutical composition comprising at least one compound of claim 1 in combination with a pharmaceutically acceptable carrier.

7. A pharmaceutical composition comprising at least one compound of claim 2 in combination with a pharmaceutically acceptable carrier.

8. A pharmaceutical composition comprising at least one compound of claim 3 in combination with a pharmaceutically acceptable carrier.

9. A pharmaceutical composition comprising at least one compound of claim 4 in combination with a pharmaceutically acceptable carrier.

10. A pharmaceutical composition comprising at least one compound of claim 5 in combination with a pharmaceutically acceptable carrier.

* * * * *